(12) United States Patent
Kimura et al.

(10) Patent No.: US 7,838,669 B2
(45) Date of Patent: Nov. 23, 2010

(54) NAPHTHALOCYANINE DYE AND METHOD FOR PRODUCING THE SAME

(75) Inventors: Keizou Kimura, Kanagawa (JP); Katsuyoshi Yamakawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 831 days.

(21) Appl. No.: 11/529,422

(22) Filed: Sep. 29, 2006

(65) Prior Publication Data
US 2007/0073053 A1 Mar. 29, 2007

(30) Foreign Application Priority Data
Sep. 29, 2005 (JP) ............................. 2005-283212

(51) Int. Cl.
*C07B 47/00* (2006.01)
*C07D 487/22* (2006.01)
(52) U.S. Cl. ................................................ 540/145
(58) Field of Classification Search .................. 540/145
See application file for complete search history.

(56) References Cited

FOREIGN PATENT DOCUMENTS

| JP | 02-296885 | 12/1990 |
|---|---|---|
| JP | 11-152413 | 6/1999 |
| JP | 11-152414 | 6/1999 |
| JP | 11-152415 | 6/1999 |

OTHER PUBLICATIONS

Michael J. Cook, et al "Octa-alkoxy Phthalocyanine and Naphthalocyanine Derivatives: Dyes with Q-Band Absorption in the Far Red or Near Infrared", J. Chem. Soc. Perkin Trans. I, pp. 2453-2458, 1988.

*Primary Examiner*—James O. Wilson
*Assistant Examiner*—Paul V. Ward
(74) *Attorney, Agent, or Firm*—Sughrue Mion, PLLC

(57) ABSTRACT

A compound of the following formula (I):

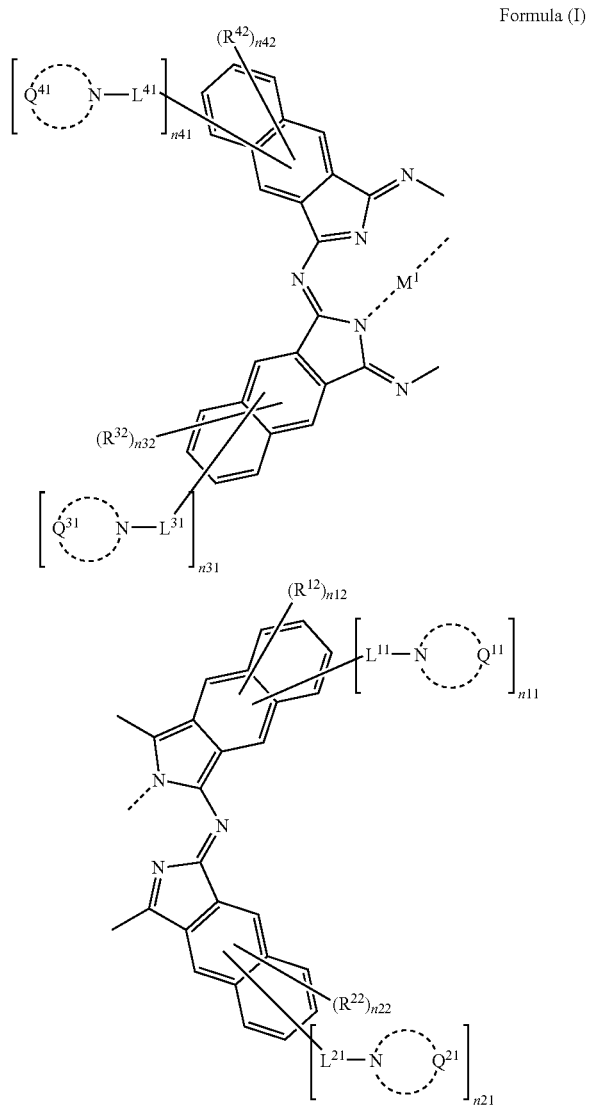

Formula (I)

wherein $L^{11}$, $L^{21}$, $L^{31}$ and $L^{41}$ represent a divalent group; $Q^{11}$, $Q^{21}$, $Q^{31}$ and $Q^{41}$ represent a non-metallic atomic group necessary for forming a hetero ring; $R^{12}$, $R^{22}$, $R^{32}$ and $R^{42}$ represent a substituent; n11, n12, n21, n22, n31, n32, n41 and n42 indicate an integer of from 0 to 6; provided that (n11+n21+n31+n41) is not 0; $M^1$ represents two hydrogen atoms, two monovalent metal atoms, a divalent metal atom, or a divalent substituted metal atom including a trivalent or tetravalent metal atom.

13 Claims, No Drawings

NAPHTHALOCYANINE DYE AND METHOD FOR PRODUCING THE SAME

BACKGROUND OF THE INVENTION

1. Field of the Invention

The present invention relates to a naphthalocyanine dye useful for image-forming materials, IR-sensitive thermal recording materials, optical recording devices and optical film materials, and more precisely, it relates to a novel naphthalocyanine dye having excellent absorption characteristics. The invention also relates to a method for producing the naphthalocyanine dye and a material for producing it.

2. Description of the Related Art

Phthalocyanines have been widely used as pigments, and among them, in particular, naphthalocyanine dyes have been much studied as near-IR dyes not substantially absorbing visible light but absorbing IR light (for example, see JP-A-2-296885).

Heretofore known are naphthalocyanine dyes having, on the naphthalene ring thereof, a substituent of a halogen atom, a carbon-bonding substituent (e.g., alkyl group, aryl group), an oxygen-bonding substituent (e.g., hydroxy group, alkoxy group, aryloxy group), a sulfur-bonding substituent (e.g., alkylthio group, arylthio group), a nitrogen-bonding substituent (e.g., amino group, alkylamino group), a carbonyl-bonding substituent (e.g., oxycarbonyl group, alkoxycarbonyl group), a nitrile group and a nitro group (for example, see JP-A-2-296885, Journal of Chemical Society, Parkin Transaction, I, pp. 2453-2458 (1988)); those having an acrylamido group as a polymerization precursor (for example, see JP-A-7-118723); and those having an acylamino group or its precursor (for example, see JP-A-11-152413, JP-A-11-152414 and JP-A-11-152415). However, heretofore unknown are naphthalocyanine dyes having a substituent with two divalent or trivalent hetero atoms bonding to each other.

SUMMARY OF THE INVENTION

An object of the invention is to provide a novel naphthalocyanine dye useful for image-forming materials, IR-sensitive thermal recording materials, optical recording devices and optical film materials. Another object of the invention is to provide a simple method for producing the naphthalocyanine dye, and to provide a starting material compound for producing it.

We, the present inventors have assiduously studied and, as a result, have found that the objects of the invention can be attained by the following means:

(1) A compound of the following formula (I):

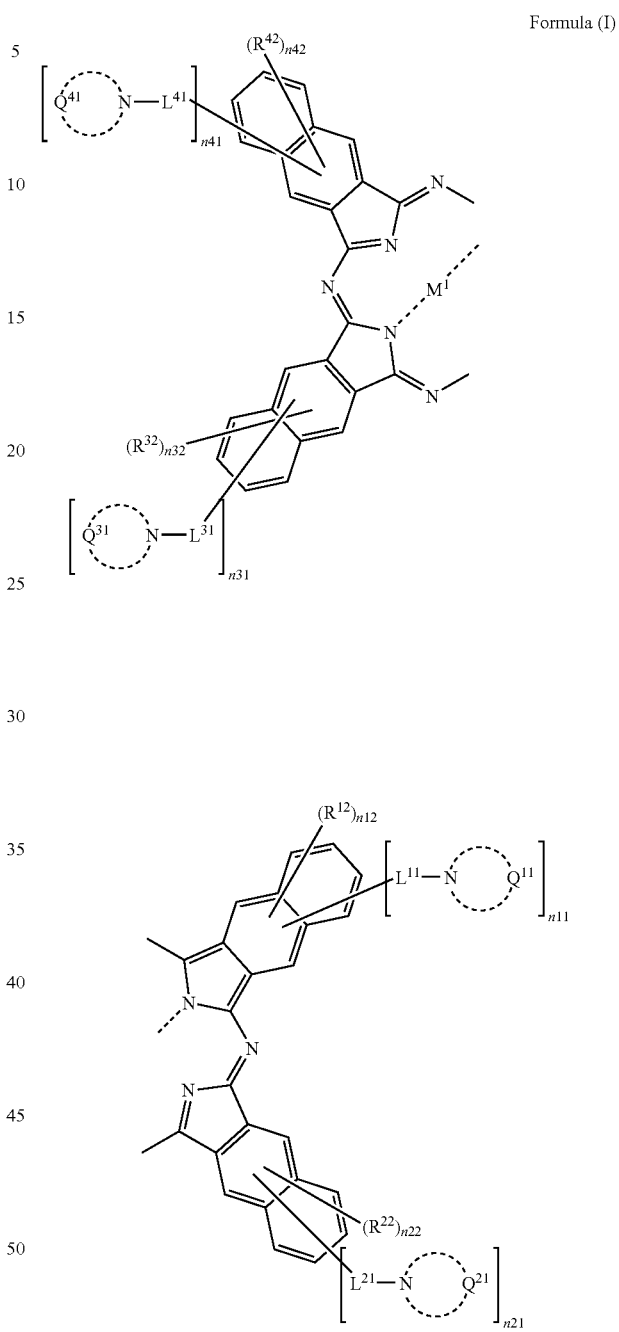

wherein $L^{11}$, $L^{21}$, $L^{31}$ and $L^{41}$ each independently represents a divalent group; $Q^{11}$, $Q^{21}$, $Q^{31}$ and $Q^{41}$ each independently represents a non-metallic atomic group necessary for forming a hetero ring along with the nitrogen atom thereof; $R^{12}$, $R^{22}$, $R^{32}$ and $R^{42}$ each independently represents a substituent; n11, n12, n21, n22, n31, n32, n41 and n42 each independently indicates an integer of from 0 to 6; provided that (n11+n21+n31+n41) is not 0; $M^1$ represents two hydrogen atoms, two monovalent metal atoms, a divalent metal atom, or a divalent substituted metal atom including a trivalent or tetravalent metal atom.

(2) A compound of the following formula (II) or (III):

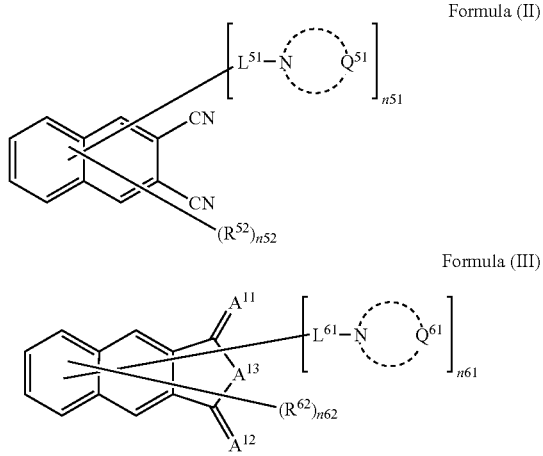

Formula (II)

Formula (III)

wherein $L^{51}$ and $L^{61}$ each independently represents a divalent group; $Q^{51}$ and $Q^{61}$ each independently represents a non-metallic atomic group necessary for forming a hetero ring along with the nitrogen atom thereof; $R^{52}$ and $R^{62}$ each independently represents a substituent; n51 and n61 each independently indicates an integer of from 1 to 6; n52 and n62 each independently indicates an integer of from 0 to 5; $A^{11}$, $A^{12}$ and $A^{13}$ each independently represents an oxygen atom or NH.

(3) A method for producing a compound of formula (I), comprising converting a compound of formula (II) or (III) to the compound of formula (I).

(4) A compound of the following formula (IV):

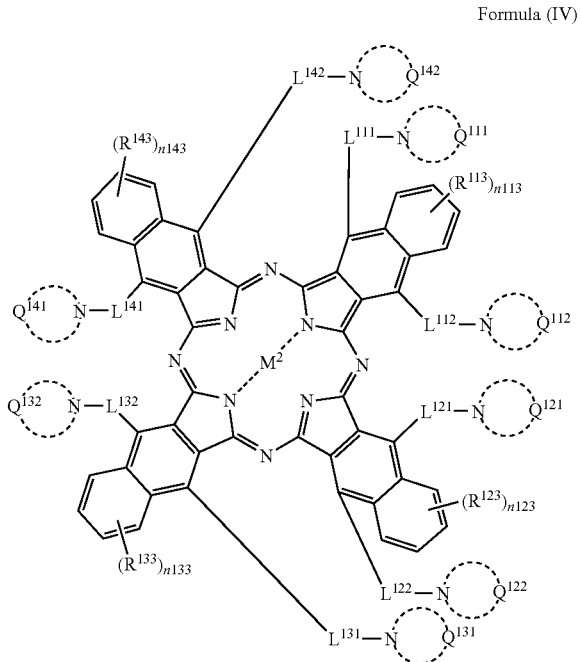

Formula (IV)

wherein $L^{111}$, $L^{112}$, $L^{121}$, $L^{122}$, $L^{131}$, $L^{132}$, $L^{141}$ and $L^{142}$ each independently represents a divalent group; $Q^{111}$, $Q^{112}$, $Q^{121}$, $Q^{122}$, $Q^{131}$, $Q^{132}$, $Q^{141}$ and $Q^{142}$ each independently represents a non-metallic atomic group necessary for forming a hetero ring along with the nitrogen atom thereof; $R^{113}$, $R^{123}$, $R^{133}$ and $R^{143}$ each independently represents a substituent; n113, n123, n133 and n143 each independently indicates an integer of from 0 to 4; $M^2$ represents two hydrogen atoms, two monovalent metal atoms, a divalent metal atom, or a divalent substituted metal atom including a trivalent or tetravalent metal atom.

(5) A compound of the following formula (V) or (VI):

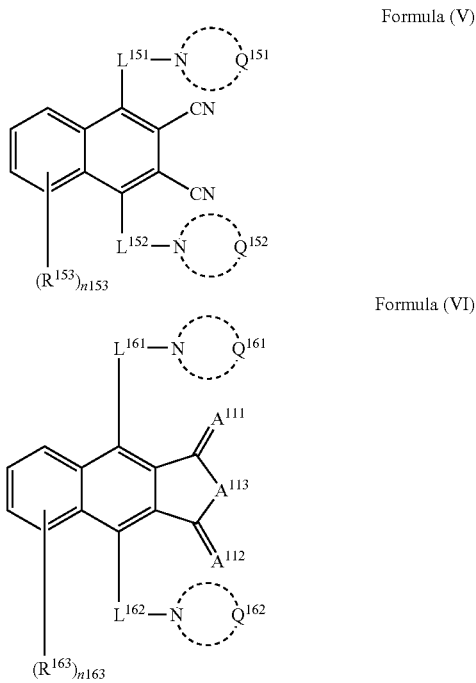

Formula (V)

Formula (VI)

wherein $L^{151}$, $L^{152}$, $L^{161}$ and $L^{162}$ each independently represents a divalent group; $Q^{151}$, $Q^{152}$, $Q^{161}$ and $Q^{162}$ each independently represents a non-metallic atomic group necessary for forming a hetero ring along with the nitrogen atom thereof; $R^{153}$ and $R^{163}$ each independently represents a substituent; n153 and n163 each independently indicates an integer of from 0 to 4; $A^{111}$, $A^{112}$ and $A^{113}$ each independently represents an oxygen atom or NH.

(6) A method for producing a compound of formula (IV), comprising converting a compound of formula (V) or (VI) to the compound of formula (IV).

DESCRIPTION OF THE PREFERRED EMBODIMENTS

The invention provides the novel naphthalocyanine dye useful for image-forming materials, IR-sensitive thermal recording materials, optical recording devices and optical film materials. The naphthalocyanine dye can be produced according to the simple method of the invention, using the starting material compound of the invention.

The compounds of the invention are described in detail hereinunder. The description of the constitutive elements of the invention given hereinunder may be for some typical embodiments of the invention, to which, however, the invention should not be limited. In this description, the numerical range expressed by the wording "a number to another number" means the range that falls between the former number indicating the lowermost limit of the range and the latter number indicating the uppermost limit thereof.

The definitions of the substituents in this description are described.

In this description, an aliphatic group is meant to include an alkyl group, a substituted alkyl group, an alkenyl group, a substituted alkenyl group, an alkynyl group, a substituted alkynyl group, an aralkyl group and a substituted aralkyl group. The alkyl group may be branched or may form a ring (that it, a cycloalkyl group). Preferably, the number of the carbon atoms constituting the alkyl group is from 1 to 20, more preferably from 1 to 18. The alkyl moiety of the substituted alkyl group may be the same as the alkyl group. The alkenyl group may be branched or may form a ring (that it, a cycloalkenyl group). Preferably, the number of the carbon atoms constituting the alkenyl group is from 2 to 20, more preferably from 2 to 18. The alkenyl moiety of the substituted alkenyl group may be the same as the alkenyl group. The alkynyl group may be branched or may form a ring (that it, a cycloalkynyl group). Preferably, the number of the carbon atoms constituting the alkynyl group is from 2 to 20, more preferably from 2 to 18. The alkynyl moiety of the substituted alkynyl group may be the same as the alkynyl group. The alkyl moiety of the aralkyl group and the substituted aralkyl group may be the same as the alkyl group. The aryl moiety of the aralkyl group and the substituted aralkyl group may be the same as the aryl group mentioned below.

The substituent of the substituted alkyl group, the substituted alkenyl group, the substituted alkynyl group and the alkyl moiety of the substituted aralkyl group includes, for example, a halogen atom (e.g., chlorine atom, bromine atom, iodine atom), an alkyl group [this means a linear, branched or cyclic, substituted or unsubstituted alkyl group, including an alkyl group (preferably an alkyl group having from 1 to 30 carbon atoms, such as a methyl group, an ethyl group, an n-propyl group, an isopropyl group, a tert-butyl group, an n-octyl group, an eicosyl group, a 2-chloroethyl group, a 2-cyano ethyl group, a 2-ethylhexyl group), a cycloalkyl group (preferably a substituted or unsubstituted cycloalkyl group having from 3 to 30 carbon atoms, such as a cyclohexyl group, a cyclopentyl group, a 4-n-dodecylcyclohexyl group), a bicycloalkyl group (preferably a substituted or unsubstituted bicycloalkyl group having from 5 to 30 carbon atoms, or that is, a monovalent group derived from a bicycloalkane having from 5 to 30 carbon atoms, by removing one hydrogen atom from it, such as a bicyclo[1.2.2]heptan2-yl group, a bicyclo[2.2.2]octan-3-yl group), and a tricyclo-structured or more multicyclo-structured group—the term "alkyl group" in the substituents to be given in the following description (for example, the alkyl group of an alkylthio group) shall have the same conception of "alkyl" as above], an alkenyl group [this means a linear, branched or cyclic, substituted or unsubstituted alkenyl group, including an alkenyl group (preferably a substituted or unsubstituted alkenyl group having from 2 to 30 carbon atoms, such as a vinyl group, an allyl group, a prenyl group, a geranyl group, an oleyl group), a cycloalkenyl group (preferably a substituted or unsubstituted cycloalkenyl group having from 3 to 30 carbon atoms, or that is, a monovalent group derived from a cycloalkene having from 3 to 30 carbon atoms, by removing one hydrogen atom from it, such as a 2-cyclopenten-1-yl group, a 2-cyclohexen-1-yl group), a bicycloalkenyl group (a substituted or unsubstituted bicycloalkenyl group, preferably a substituted or unsubstituted bicycloalkenyl group having from 5 to 30 carbon atoms, or that is, a monovalent group derived from a bicycloalkene having one double bond, by removing one hydrogen atom from it, such as a bicyclo[2.2.1]hept-2-en-1-yl group, a bicy-clo[2.2.2]oct-2-en-4-yl group)], an alkynyl group (preferably a substituted or unsubstituted alkynyl group having from 2 to 30 carbon atoms, such as an ethynyl group, a propargyl group, a trimethylsilylethynyl group), an aryl group (preferably a substituted or unsubstituted aryl group having from 6 to 30 carbon atoms, such as a phenyl group, a p-tolyl group, a naphthyl group, an m-chlorophenyl group, an o-hexadecanoylaminophenyl group), a heterocyclic group (preferably a monovalent group derived from 5- or 6-membered, substituted or unsubstituted, aromatic or nonaromatic heterocyclic compound, by removing one hydrogen atom from it, more preferably a 5- or 6-membered aromatic heterocyclic group having from 3 to 30 carbon atoms, such as a 2-furyl group, a 2-thienyl group, a 2-pyrimidinyl group, a 2-benzothiazolyl group), a cyano group, a hydroxyl group, a nitro group, a carboxyl group, an alkoxy group (preferably a substituted or unsubstituted alkoxy group having from 1 to 30 carbon atoms, such as a methoxy group, an ethoxy group, an isopropoxy group, a tert-butoxy group, an n-octyloxy group, a 2-methoxyethoxy group), an aryloxy group (preferably a substituted or unsubstituted aryloxy group having from 6 to 30 carbon atoms, such as a phenoxy group, a 2-methylphenoxy group, a 4-tert-butylphenoxy group, a 3-nitrophenoxy group, a 2-tetradecanoylaminophenoxy group), a silyloxy group (preferably a silyloxy group having from 3 to 20 carbon atoms, such as a trimethylsilyloxy group, a tert-butyldimethylsilyloxy group), a heterocyclic-oxy group (preferably a substituted or unsubstituted heterocyclic-oxy group having from 2 to 30 carbon atoms, such as a 1-phenyltetrazolyl-5-oxy group, a 2-tetrahydropyranyloxy group), an acyloxy group (preferably a formyloxy group, a substituted or unsubstituted alkylcarbonyloxy group having from 2 to 30 carbon atoms, a substituted or unsubstituted arylcarbonyloxy group having from 6 to 30 carbon atoms, for example, a formyloxy group, an acetyloxy group, a pivaloyloxy group, a stearoyloxy group, a benzoyloxy group, a p-methoxyphenylcarbonyloxy group), a carbamoyloxy group (preferably a substituted or unsubstituted carbamoyloxy group having from 1 to 30 carbon atoms, such as an N,N-dimethylcarbamoyloxy group, an N,N-diethylcarbamoyloxy group, a morpholinocarbonyloxy group, an N,N-di-n-octylaminocarbonyloxy group, an N-n-octylcarbamoyloxy group), an alkoxycarbonyloxy group (preferably a substituted or unsubstituted alkoxycarbonyloxy group having from 2 to 30 carbon atoms, such as a methoxycarbonyloxy group, an ethoxycarbonyloxy group, a tert-butoxycarbonyloxy group, an n-octylcarbonyloxy group), an aryloxycarbonyloxy group (preferably a substituted or unsubstituted aryloxycarbonyloxy group having from 7 to 30 carbon atoms, such as a phenoxycarbonyloxy group, a p-methoxyphenoxycarbonyloxy group, a p-n-hexadecyloxyphenoxycarbonyloxy group), an amino group (preferably an amino group, a substituted or unsubstituted alkylamino group having from 1 to 30 carbon atoms, a substituted or unsubstituted anilino group having from 6 to 30 carbon atoms, for example, an amino group, a methylamino group, a dimethylamino group, an anilino group, an N-methylanilino group, a diphenylamino group), an acylamino group (preferably a formylamino group, a substituted or unsubstituted alkylcarbonylamino group having from 1 to 30 carbon atoms, a substituted or unsubstituted arylcarbonylamino group having from 6 to 30 carbon atoms, for example, a formylamino group, an acetylamino group, a pivaloylamino group, a lauroylamino group, a benzoylamino group, a 3,4,5-tri-n-octyloxyphenylcarbonylamino group), an aminocarbonylamino group (preferably a substituted or unsubstituted aminocarbonylamino group having from 1 to 30 carbon atoms, such as a carbamoylamino group, an N,N-dimethylaminocarbonylamino group, an N,N-diethylaminocarbonylamino group, a morpholinocarbonylamino group), an alkoxycarbonylamino group (preferably a substituted or unsubstituted alkoxycarbonylamino group having from 2 to 30 carbon atoms, such as a methoxycarbonylamino group, an ethoxycarbonylamino group, a tert-butoxycarbonylamino group, an n-octadecyloxycarbonylamino group, an N-methyl-methoxycarbonylamino group), an aryloxycarbonylamino group (preferably a substituted or unsubstituted aryloxycarbonylamino group having from 7 to 30 carbon atoms, such as a phenoxycarbonylamino group, a p-chlorophenoxycarbonylamino group, an m-n-octyloxyphenoxycarbonylamino group), a sulfamoylamino group (preferably a substituted or unsubstituted sulfamoylamino group having from 0 to 30 carbon atoms, such as a sulfamoylamino group, an N,N-dimethylaminosulfonylamino group, an N-n-octylaminosulfonylamino group), an alkyl or arylsulfonylamino group (preferably a substituted or unsubstituted alkylsulfonylamino group having from 1 to 30 carbon atoms, a substituted or unsubstituted arylsulfonylamino group having from 6 to 30 carbon atoms, such as a methylsulfonylamino group, a butylsulfonylamino group, a phenylsulfonylamino group, a 2,3,5-trichlorophenylsulfonylamino group, a p-methylphenylsulfonylamino group), a mercapto group, an alkylthio group (preferably a substituted or unsubstituted alkylthio group having from 1 to 30 carbon atoms, such as a methylthio group, an ethylthio group, an n-hexadecylthio group), an arylthio group (preferably a substituted or unsubstituted arylthio group having from 6 to 30 carbon atoms, such as a phenylthio group, a p-chlorophenylthio group, an m-methoxyphenylthio group), a heterocyclic-thio group (preferably a substituted or unsubstituted heterocyclic-thio group having from 2 to 30 carbon atoms, such as a 2-benzothiazolylthio group, a 1-phenyltetrazol-5-ylthio group), a sulfamoyl group (preferably a substituted or unsubstituted sulfamoyl group having from 0 to 30 carbon atoms, such as an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N'-phenylcarbamoyl)sulfamoyl group), a sulfo group, an alkyl or arylsulfinyl group (preferably a substituted or unsubstituted alkylsulfinyl group having from 1 to 30 carbon atoms, a substituted or unsubstituted arylsulfinyl group having from 6 to 30 carbon atoms, such as a methylsulfinyl group, an ethylsulfinyl group, a phenylsulfinyl group, a p-methylphenylsulfinyl group), an alkyl or arylsulfonyl group (preferably a substituted or unsubstituted alkylsulfonyl group having from 1 to 30 carbon atoms, a substituted or unsubstituted arylsulfonyl group having from 6 to 30 carbon atoms, such as a methylsulfonyl group, an ethylsulfonyl group, a phenylsulfonyl group, a p-methylphenylsulfonyl group), an acyl group (preferably a formyl group, a substituted or unsubstituted alkylcarbonyl group having from 2 to 30 carbon atoms, a substituted or unsubstituted arylcarbonyl group having from 7 to 30 carbon atoms, a substituted or unsubstituted heterocyclic-carbonyl group having from 4 to 30 carbon atoms and bonding to the carbonyl group via the carbon atom thereof, for example, an acetyl group, a pivaloyl group, a 2-chloroacetyl group, a stearoyl group, a benzoyl group, a p-n-octyloxyphenylcarbonyl group, a 2-pyridylcarbonyl group, a 2-furylcarbonyl group), an aryloxycarbonyl group (preferably a substituted or unsubstituted aryloxycarbonyl group having from 7 to 30 carbon atoms, such as a phenoxycarbonyl group, an o-chlorophenoxycarbonyl group, an m-nitrophenoxycarbonyl group, a p-tert-butylphenoxycarbonyl group), an alkoxycarbonyl group (preferably a substituted or unsubstituted alkoxycarbonyl group having from 2 go 30 carbon atoms, such as a methoxycarbonyl group, an ethoxycarbonyl group, a tert-butoxycarbonyl group, an n-octadecyloxycarbonyl group), a carbamoyl group (preferably a substituted or unsubstituted carbamoyl group having from 1 to 30 carbon atoms, such as a carbamoyl group, an N-methylcarbamoyl group, an N,N-dimethylcarbamoyl group, an N,N-di-n-octylcarbamoyl group, an N-(methylsulfonyl)carbamoyl group), an aryl or heterocyclic-azo group (preferably a substituted or unsubstituted arylazo group having from 6 to 30 carbon atoms, a substituted or unsubstituted heterocyclic-azo group having from 3 to 30 carbon atoms, such as a phenylazo group, a p-chlorophenylazo group, a 5-ethylthio-1,3,4-thiadiazol-2-ylazo group), an imido group (preferably an N-succinimido group, an N-phthalimido group), a phosphino group (preferably a substituted or unsubstituted phosphino group having from 2 to 30 carbon atoms, such as a dimethylphosphino group, a diphenylphosphino group, a methylphenoxyphosphino group), a phosphinyl group (preferably a substituted or unsubstituted phosphinyl group having from 2 to 30 carbon atoms, such as a phosphinyl group, a dioctyloxyphosphinyl group, a diethoxyphosphinyl group), a phosphinyloxy group (preferably a substituted or unsubstituted phosphinyloxy group having from 2 to 30 carbon atoms, such as a diphenoxyphosphinyloxy group, a dioctyloxyphosphinyloxy group), a phosphinylamino group (preferably a substituted or unsubstituted phosphinylamino group having from 2 to 30 carbon atoms, such as a dimethoxyphosphinylamino group, a dimethylaminophosphinylamino group), a silyl group (preferably a substituted or unsubstituted silyl group having from 3 to 30 carbon atoms, such as a trimethylsilyl group, a tert-butyldimethylsilyl group, a phenyldimethylsilyl group).

Of the above-mentioned functional groups, those having a hydrogen atom may be further substituted with any of the above-mentioned groups, by removing the hydrogen atom. Examples of the functional groups of the type include an alkylcarbonylaminosulfonyl group, an arylcarbonylaminosulfonyl group, an alkylsulfonylaminocarbonyl group, an arylsulfonylaminocarbonyl group. Their examples are a methylsulfonylaminocarbonyl group, a p-methylphenylsulfonylaminocarbonyl group, an acetylaminosulfonyl group, a benzoylaminosulfonyl group. The substituent in the aryl moiety of the substituted. aralkyl group may include the substituents of the substituted aryl group mentioned below.

In this description, the aromatic group means an aryl group and a substituted aryl group. The aromatic group may be condensed with an aliphatic ring, any other aromatic ring or a hetero ring. Preferably, the number of the carbon atoms constituting the aromatic group is from 6 to 40, more preferably from 6 to 30, even more preferably from 6 to 20. Of those, the aryl group is preferably a phenyl group or a naphthyl group, more preferably a phenyl group.

The aryl moiety of the substituted aryl group may be the same as the above-mentioned aryl group. The substituent of the substituted aryl group includes the substituents mentioned hereinabove for the substituent of the substituted alkyl group, the substituted alkenyl group, the substituted alkynyl group, and the alkyl moiety of the substituted aralkyl group.

The compounds of formulae (I) to (VI) are described below.

In formula (I), $L^{11}$, $L^{21}$, $L^{31}$ and $L^{41}$ each independently represents a divalent group; preferably —O—, —N($R^{211}$)—, —S—, —C($R^{212}$)($R^{213}$)—, —CO—, —CO—N($R^{214}$)—, —SO—, —SO$_2$—, —SO$_2$N($R^{215}$), or a group of their combinations; more preferably a group of one or more their combinations; even more preferably a group of one of them; still more preferably a group of —O—, —N($R^{211}$)—, —S—, —SO—, —SO$_2$— or —SO$_2$N($R^{215}$); further more preferably a group of —O—, —N($R^{211}$)— or —S—. In these, $R^{211}$, $R^{212}$, $R^{213}$, $R^{214}$ and $R^{215}$ each represent a hydrogen atom, an aliphatic group, an aromatic group or a heterocyclic group. Preferably, $R^{211}$, $R^{212}$, $R^{213}$, $R^{214}$ and $R^{215}$ each are a hydrogen atom, an aliphatic group having from 1 to 20 carbon atoms, an aromatic group having from 6 to 20 carbon atoms, or a heterocyclic group having from 4 to 20 carbon atoms; more preferably a hydrogen atom, an alkyl group having from 1 to 10 carbon atoms, or a phenyl group having from 6 to 10 carbon atoms; even more preferably a hydrogen atom, or an alkyl group having from 1 to 6 carbon atoms; most preferably a hydrogen atom.

$Q^{11}$, $Q^{21}$, $Q^{31}$ and $Q^{41}$ each independently represents a non-metallic atomic group necessary for forming a hetero ring along with the nitrogen atom thereof. The hetero ring is preferably a 5-membered or 6-membered ring, more preferably a 5-membered ring. Also preferably, the hetero ring is a nitrogen atom-containing, saturated or unsaturated hetero ring, and the hetero ring has a free atomic valence (monovalent) at its nitrogen atom (the hetero ring bonds to the compound via the nitrogen atom). The hetero atom except the nitrogen atom via which the hetero ring bonds to the compound includes B, N, O, S, Se and Te. The hetero atom is preferably N, O and S. The hetero ring may be condensed with an aliphatic ring, an aromatic ring or any other hetero ring. Preferably, the number of the carbon atoms constituting the heterocyclic group is from 1 to 40, more preferably from 1 to 30, even more preferably from 1 to 20. Examples of the saturated hetero ring include a pyrrolidine ring, a morpholine ring and a 1,3-thiazolidine ring. Examples of the unsaturated hetero ring include a thiazole ring, an oxazole ring, a selenazole ring, an imidazole ring, a pyrazole ring, a benzimidazole ring, an indole ring, a benzotriazole ring, a benzothiazole ring, a benzoxazole ring and a purine ring. The heterocyclic ring may have a substituent. Examples of the substituent include the substituents mentioned hereinabove for the substituent of the substituted alkyl group, the substituted alkenyl group, the substituted alkynyl group and the alkyl moiety of the substituted aralkyl group.

$R^{12}$, $R^{22}$, $R^{32}$ and $R^{42}$ each independently represents a substituent. Examples of the substituent include the substituents mentioned hereinabove for the substituent of the substituted alkyl group, the substituted alkenyl group, the substituted alkynyl group and the alkyl moiety of the substituted aralkyl group. In case where the compound has plural $R^{12}$'s, then the plural $R^{12}$'s may form a cyclic structure. The same shall apply to $R^{22}$, $R^{32}$ and $R^{42}$. Preferably, $R^{12}$, $R^{22}$, $R^{32}$ and $R^{42}$ are any of a halogen atom, an alkyl group, an alkenyl group, an alkynyl group, an aryl group, a cyano group, a hydroxyl group, a nitro group, a carboxyl group, an alkoxy group, an aryloxy group, a silyloxy group, a heterocyclic-oxy group, an acyloxy group, a carbamoyloxy group, an alkoxycarbonyloxy group, an aryloxycarbonyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic-thio group, a sulfamoyl group, a sulfo group, an alkyl or arylsulfinyl group, an alkyl or arylsulfonyl group, an acyl group, an aryloxycarbonyl group, an alkoxycarbonyl group, a carbamoyl group, an imido group, a phosphino group, a phosphinyl group, a phosphinyloxy group, a phosphinylamino group, or a silyl group; more preferably a halogen atom, an alkyl group, an aryl group, a cyano group, a hydroxyl group, a nitro group, a carboxyl group, an alkoxy group, an aryloxy group, a silyloxy group, a heterocyclic-oxy group, an acyloxy group, a carbamoyloxy group, an amino group, an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclic-thio group, a sulfamoyl group, an alkyl or arylsulfinyl group, an alkyl or arylsulfonyl group, a carbamoyl group, an imido group, a phosphino group, a phosphinyl group, a phosphinyloxy group, a phosphinylamino group, or a silyl group; even more preferably a halogen atom, an alkyl group, an aryl group, a hydroxyl group, an alkoxy group, an aryloxy group, an amino group, a mercapto group, an alkylthio group, an arylthio group, a sulfamoyl group, a sulfo group, an alkyl or arylsulfinyl group, an alkyl or arylsulfonyl group; still more preferably a halogen atom, an alkyl group, an aryl group, an alkoxy group, an aryloxy group, an alkylthio group, or an arylthio group; further more preferably a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylthio group having from 1 to 20 carbon atoms, or an arylthio group having from 6 to 20 carbon atoms; still further preferably an alkyl group having from 1 to 8 carbon atoms, an aryl group having from 6 to 10 carbon atoms, an alkoxy group having from 1 to 8 carbon atoms, an aryloxy group having from 6 to 10 carbon atoms, an alkylthio group having from 1 to 8 carbon atoms, or an arylthio group having from 6 to 10 carbon atoms; still further preferably an alkoxy group having from 1 to 6 carbon atoms, an aryloxy group having from 6 to 8 carbon atoms, an alkylthio group having from 1 to 6 carbon atoms, or an arylthio group having from 6 to 8 carbon atoms.

n11, n12, n21, n22, n31, n32, n41 and n42 each independently indicates an integer of from 0 to 6. Preferably, n11, n21, n31 and n41 are the same, indicating 1 or 2; and n12, n22, n32 and n42 are the same, indicating 0, 1 or 2. More preferably, n11, n21, n31 and n41 are the same, indicating 1 or 2; and n12, n22, n32 and n42 are the same, indicating 0 or 1. Even more preferably, n11, n21, n31 and n41 are 2; and n12, n22, n32 and n42 are the same, indicating 0 or 1. Still more preferably, n11, n21, n31 and n41 are 2; and n12, n22, n32 and n42 are 0. Most preferably, n11, n21, n31 and n41 are 2; n12, n22, n32 and n42 are 0; and the substituting positions of the hetero rings formed of $Q^{11}$, $Q^{21}$, $Q^{31}$ and $Q^{41}$ with the nitrogen atom thereof are all the same, and the rings are substituted all at the α-position of the naphthalene ring.

$M^1$ is preferably two hydrogen atoms, $Li^{+}$'s, $Na^{+}$'s, $K^{+}$'s, $Rb^{+}$'s, $Cs^{+}$'s, or $Be^{2+}$, $Mg^{2+}$, $Ca^{2+}$, $Ti^{2+}$, $Mn^{2+}$, $Fe^{2+}$, $Co^{2+}$, $Ni^{2+}$, $Cu^{2+}$, $Zn^{2+}$, $Ru^{2+}$, $Rh^{2+}$, $Pd^{2+}$, $Pt^{2+}$, $Ba^{2+}$, $Cd^{2+}$, $Hg^{2+}$, $Pb^{2+}$, $Sn^{2+}$, or Al—Cl, Al—Br, Al—F, Al—I, Ga—Cl, Ga—F, Ga—I, Ga—Br, In—Cl, In—Br, In—I, In—F, Tl—Cl, Tl—Br, Tl—I, Tl—F, Mn—OH, Fe—Cl, Ru—Cl, $CrCl_2$, $SiCl_2$, $SiBr_2$, $SiF_2$, $SiI_2$, $ZrCl_2$, $GeCl_2$, $GeBr_2$, $GeI_2$, $GeF_2$, $SnCl_2$, $SnBr_2$, $SnI_2$, $SnF_2$, $TiCl_2$, $TiBr_2$, $TiF_2$, $Si(OH)_2$, $Ge(OH)_2$, $Zr(OH)_2$, $Mn(OH)_2$, $Sn(OH)_2$, $TiR_2$, $CrR_2$, $SiR_2$, $SnR_2$, $GeR_2$, $Si(OR)_2$, $Sn(OR)_2$, $Ge(OR)_2$, $Ti(OR)_2$, $Cr(OR)_2$, $Sn(SR)_2$, $Ge(SR)_2$ [where R represents an aliphatic group, or an aromatic group], VO, MnO or TiO; more preferably, two hydrogen atoms, $Li^{+}$'s, $Na^{+}$'s, $K^{+}$'s, $Rb^{+}$'s or $Be^{2+}$, $Mg^{2+}$, $Ca^{2+}$, $Ti^{2+}$, $Mn^{2+}$, $Fe^{2+}$, $Co^{2+}$, $Ni^{2+}$, $Cu^{2+}$, $Zn^{2+}$, $Ru^{2+}$, $Rh^{2+}$, $Pd^{2+}$, $Pt^{2+}$, $Ba^{2+}$, $Sn^{2+}$, or Al—Cl, Al—Br, Ga—Cl, Ga—F, Ga—I, Ga—Br, In—Cl, In—Br, Tl—Cl, Tl—Br, Mn—OH, Fe—Cl, Ru—Cl, $CrCl_2$, $SiCl_2$, $SiBr_2$, $ZrCl_2$, $GeCl_2$, $GeBr_2$, $SnCl_2$, $SnBr_2$, $TiCl_2$, $TiBr_2$, $Si(OH)_2$, $Ge(OH)_2$, $Zr(OH)_2$, $Mn(OH)_2$, $Sn(OH)_2$, $TiR_2$, $CrR_2$, $SiR_2$, $SnR_2$, $GeR_2$, $Si(OR)_2$, $Sn(OR)_2$, $Ge(OR)_2$, $Ti(OR)_2$, $Cr(OR)_2$, $Sn(SR)_2$, $Ge(SR)_2$ [where R represents an aliphatic group, or an aromatic group], VO, MnO or TiO; even more preferably, two hydrogen atoms, Li$^+$'s, Na$^+$'s, K$^+$'s, or Be$^{2+}$, Mg$^{2+}$, Ca$^{2+}$, Ti$^{2+}$, Mn$^{2+}$, Fe$^{2+}$, Co$^{2+}$, Ni$^{2+}$, Cu$^{2+}$, Zn$^{2+}$, Ru$^{2+}$, Rh$^{2+}$, Pd$^{2+}$, Pt$^{2+}$, Ba$^{2+}$, Sn$^{2+}$, or Al—Cl, Ga—Cl, In—Cl, Tl—Cl, Mn—OH, Fe—Cl, Ru—Cl, CrCl$_2$, SiCl$_2$, ZrCl$_2$, GeCl$_2$, TiCl$_2$, Si(OH)$_2$, Ge(OH)$_2$, Zr(OH)$_2$, Mn(OH)$_2$, TiR$_2$, CrR$_2$, SiR$_2$, GeR$_2$, Si(OR)$_2$, Ge(OR)$_2$, Ti(OR)$_2$, Cr(OR)$_2$, [where R represents an aliphatic group, or an aromatic group], VO, MnO or TiO.

In formula (II), $L^{51}$, $Q^{51}$ and $R^{52}$ have the same meanings as the above-mentioned $L^{11}$, $Q^{11}$ and $R^{12}$, respectively, and their preferred ranges are also the same as those of the latter. n51 is preferably 1 or 2, more preferably 2. Even more preferably, n51 is 2, and the substituents are at the α-position adjacent to CN of the naphthalene ring. n52 is preferably from 0 to 2, more preferably 0 or 1, even more preferably 0.

In formula (III), $L^{61}$, $Q^{61}$ and $R^{62}$ have the same meanings as the above-mentioned $L^{11}$, $Q^{11}$ and $R^{12}$, respectively, and their preferred ranges are also the same as those of the latter. n61 and n62 have the same meanings as those of n51 and n52, respectively, and their preferred ranges are also the same as those of the latter. $A^{11}$, $A^{12}$ and $A^{13}$ each independently represents an oxygen atom or NH. Preferably, $A^{11}$ and $A^{12}$ are the same.

In formula (IV), $L^{111}$, $L^{112}$, $L^{121}$, $L^{122}$, $L^{131}$, $L^{132}$, $L^{141}$ and $L^{142}$ have the same meanings as those of the above-mentioned $L^{11}$, and their preferred ranges are also the same as those of the latter. $Q^{111}$, $Q^{112}$, $Q^{121}$, $Q^{122}$, $Q^{131}$, $Q^{132}$, $Q^{141}$ and $Q^{142}$ have the same meanings as those of the above-mentioned $Q^{11}$, and their preferred ranges are also the same as those of the latter. $R^{111}$, $R^{112}$, $R^{133}$ and $R^{143}$ have the same meanings as those of $R^{12}$, and their preferred ranges are also the same as those of the latter. n113, n123, n133 and n143 are preferably from 0 to 3, more preferably from 0 to 2, even more preferably 0 or 1, most preferably 0. $M^2$ has the same meaning as that of $M^1$ and its preferred range is also the same as that of the latter.

In formula (V), $L^{151}$ and $L^{152}$ have the same meanings as those of the above-mentioned $L^{11}$, and their preferred ranges are also the same as those of the latter. $Q^{151}$ and $Q^{152}$ have the same meanings as those of the above-mentioned $Q^{11}$, and their preferred ranges are also the same as those of the latter. $R^{153}$ and n153 have the same meanings as those of $R^{113}$ and n113, respectively, and their preferred ranges are also the same as those of the latter.

In formula (VI), $L^{161}$ and $L^{162}$ have the same meanings as those of the above-mentioned $L^{11}$, and their preferred ranges are also the same as those of the latter. $Q^{161}$ and $Q^{162}$ have the same meanings as those of the above-mentioned $Q^{11}$, and their preferred ranges are also the same as those of the latter. $R^{163}$ and n163 have the same meanings as those of $R^{113}$ and n113, respectively, and their preferred ranges are also the same as those of the latter. $A^{111}$, $A^{112}$ and $A^{113}$ have the same meanings as those of $A^{11}$, $A^{12}$ and $A^{13}$, and their preferred ranges are also the same as those of the latter.

Examples of the compounds of formulae (I) to (VI) of the invention are mentioned below, to which, however, the invention should not be limited.

Compounds of Formula (I) or (IV):

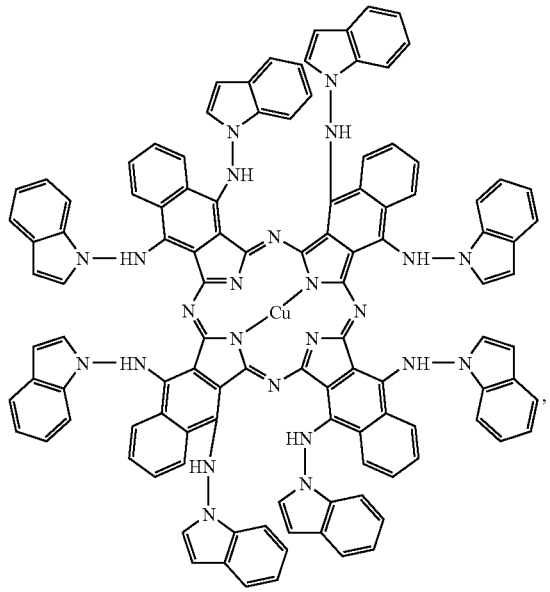

(NC-1)

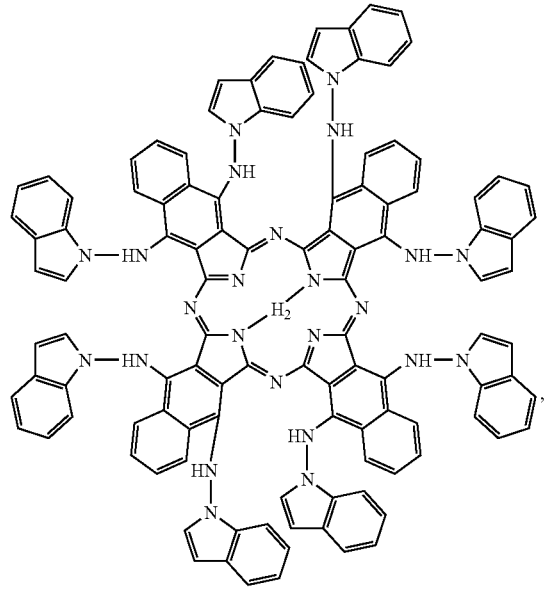

(NC-2)

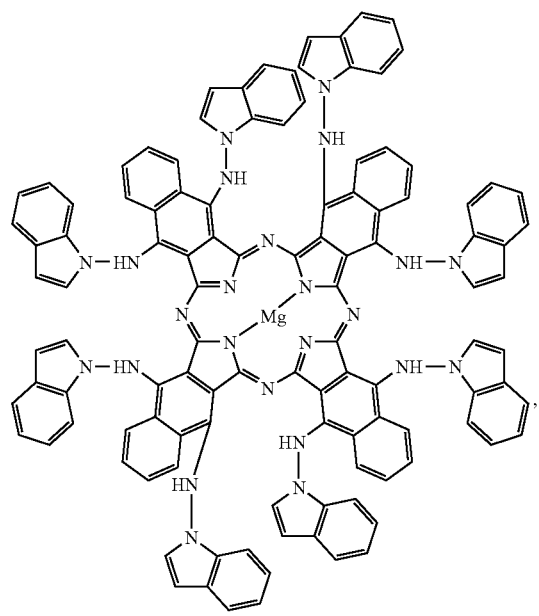
(NC-3)
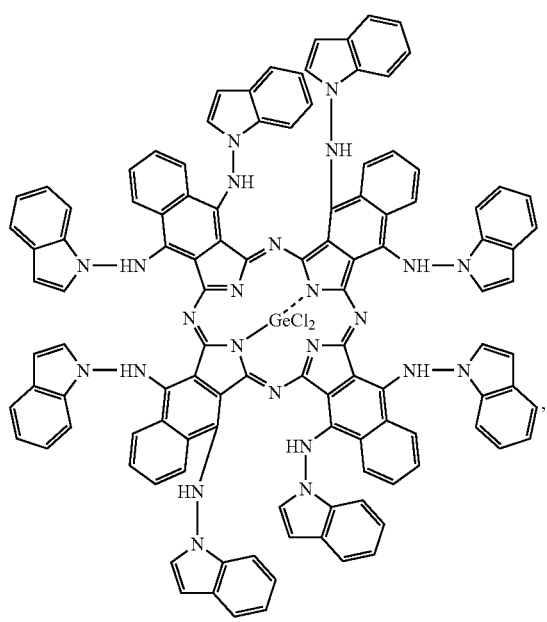
(NC-5)
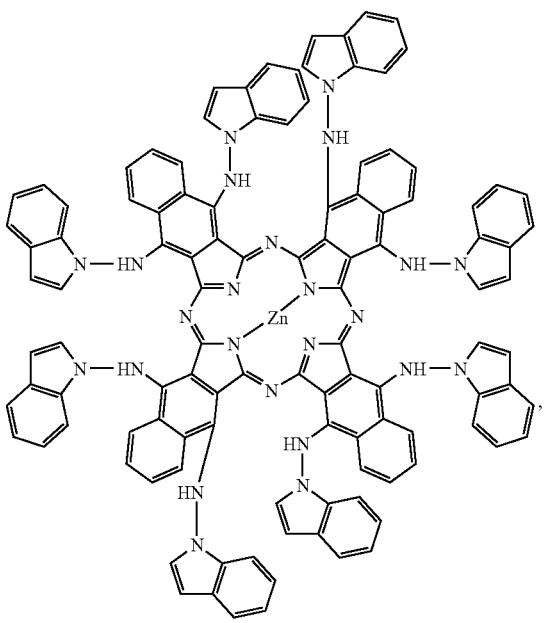
(NC-4)
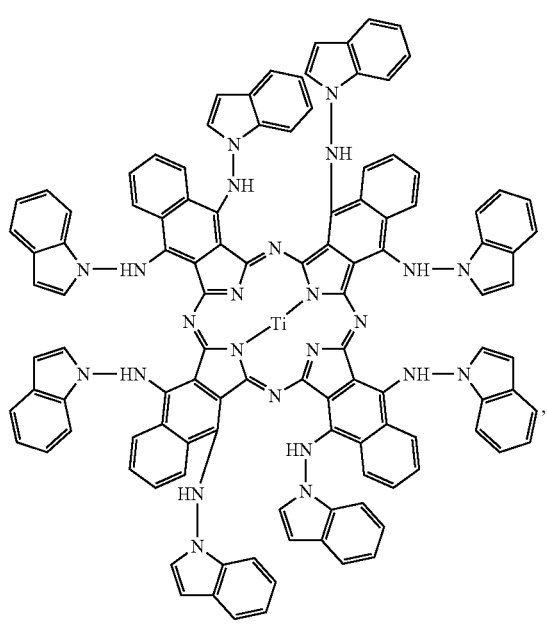
(NC-6)

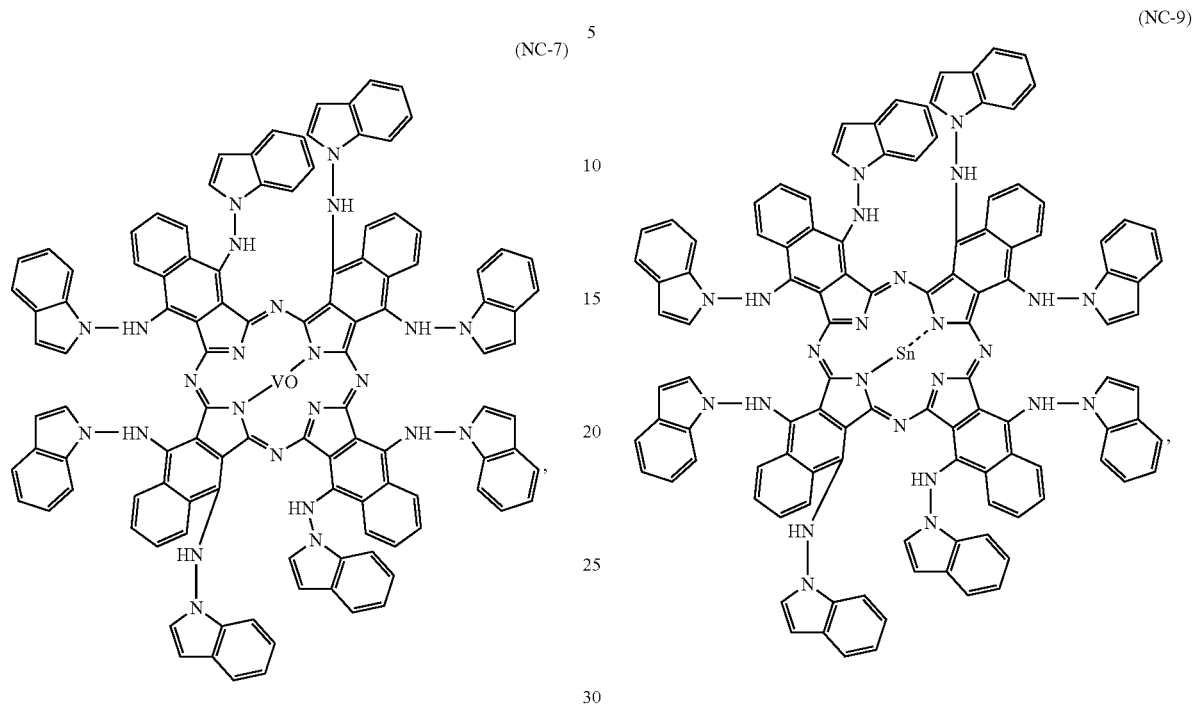
(NC-7)
(NC-9)
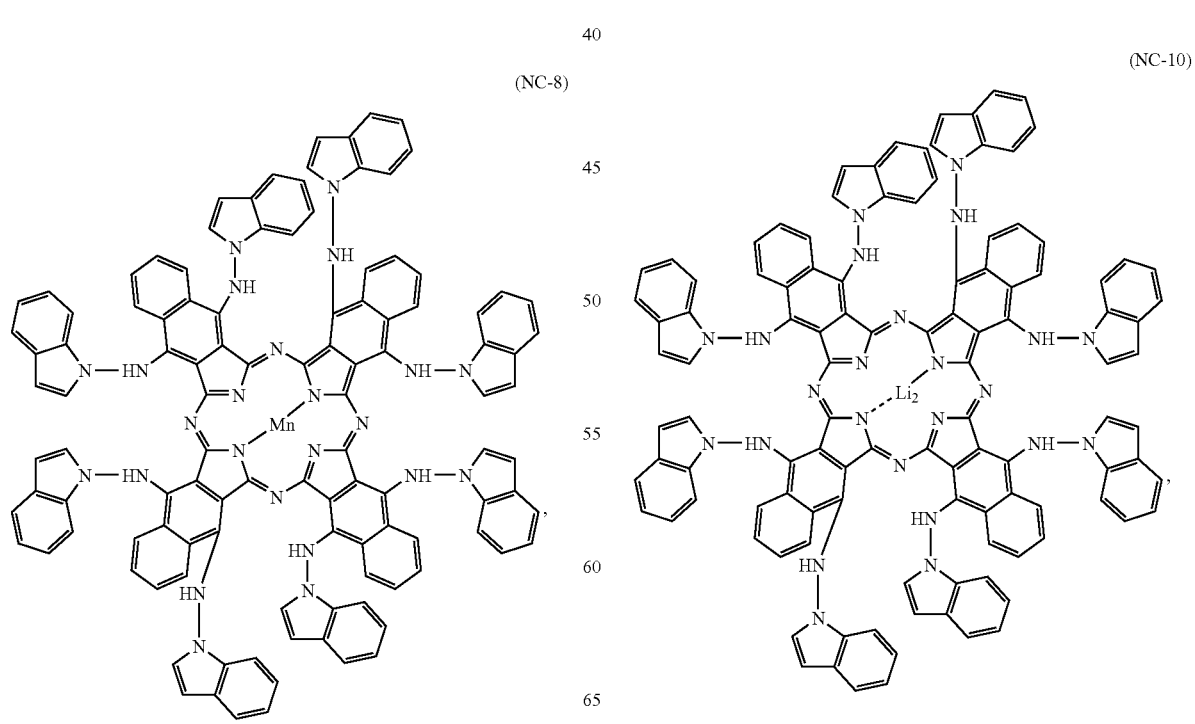
(NC-8)
(NC-10)

(NC-11)
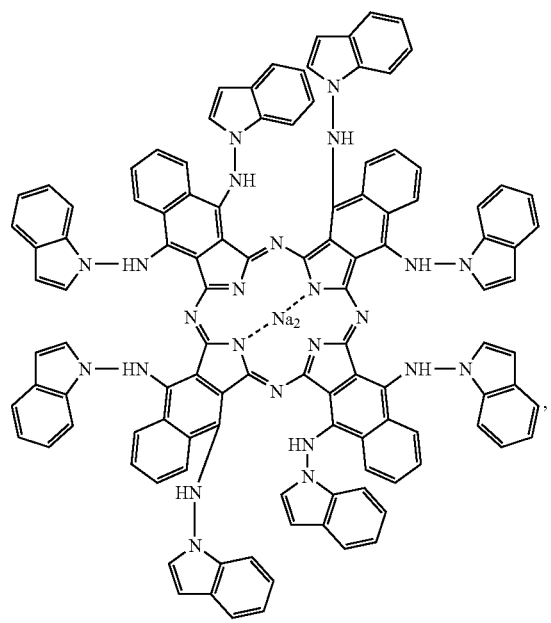
(NC-12)
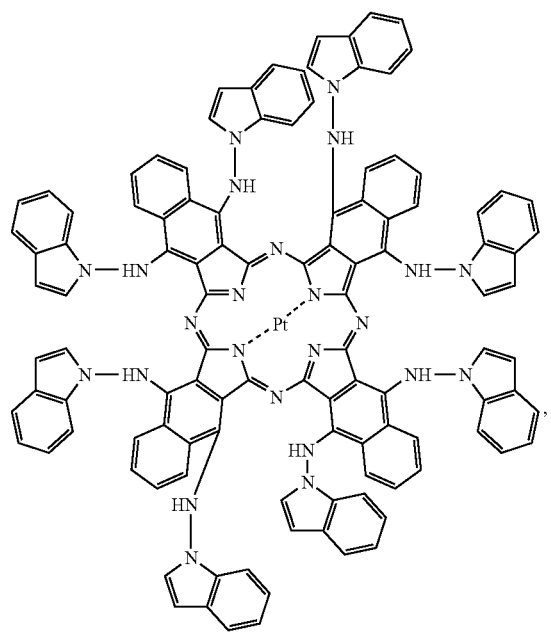
(NC-13)
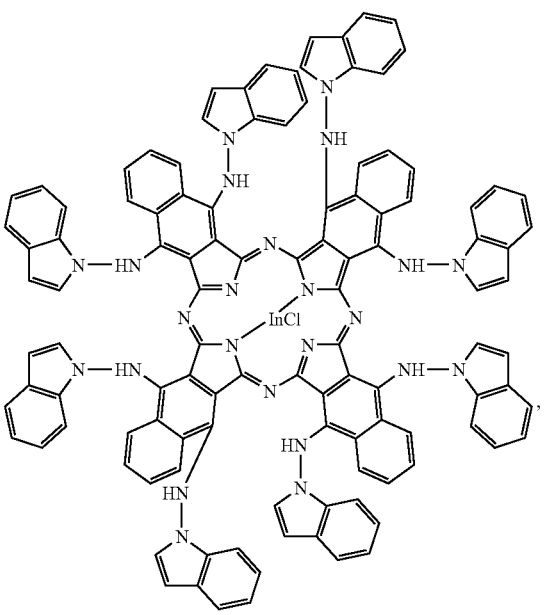
(NC-14)
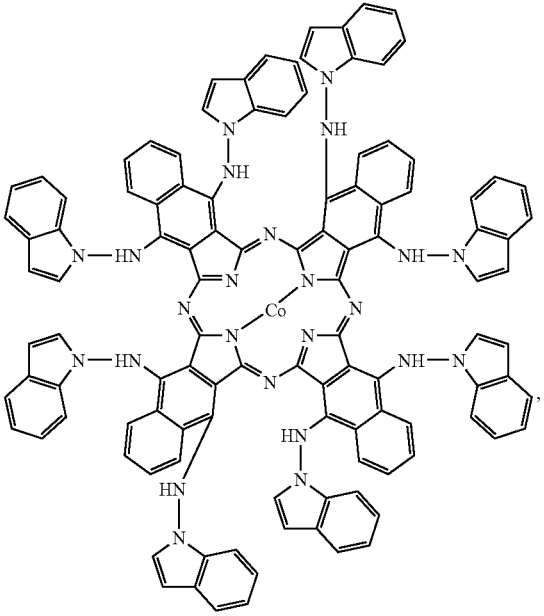

-continued
(NC-15)
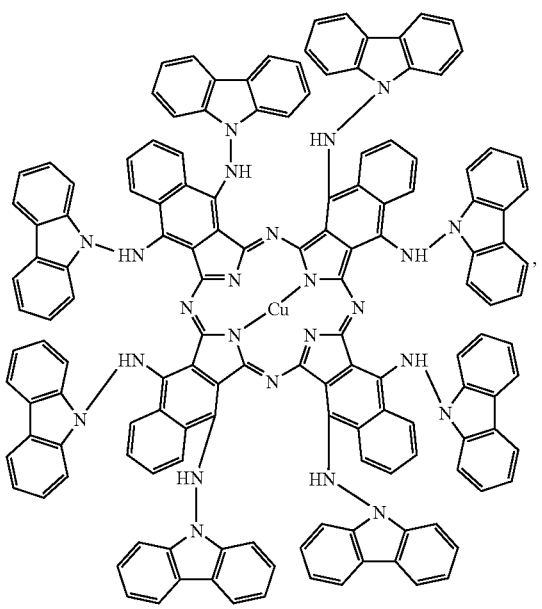
(NC-17)
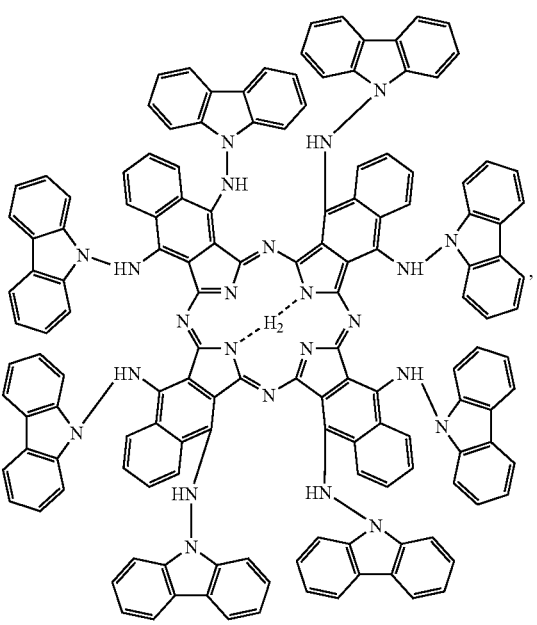
(NC-16)
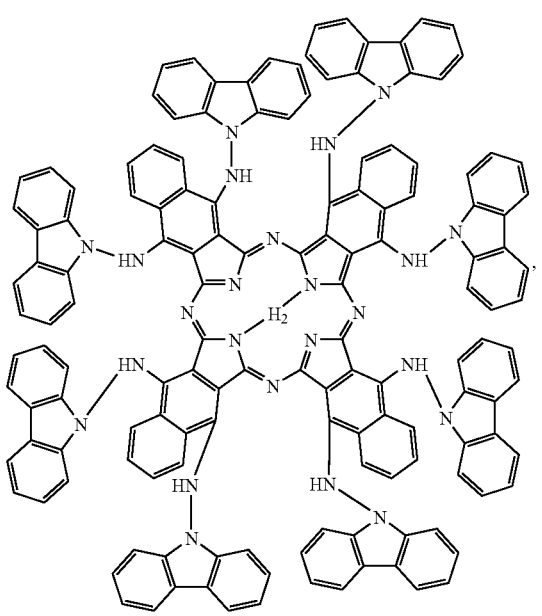
(NC-18)
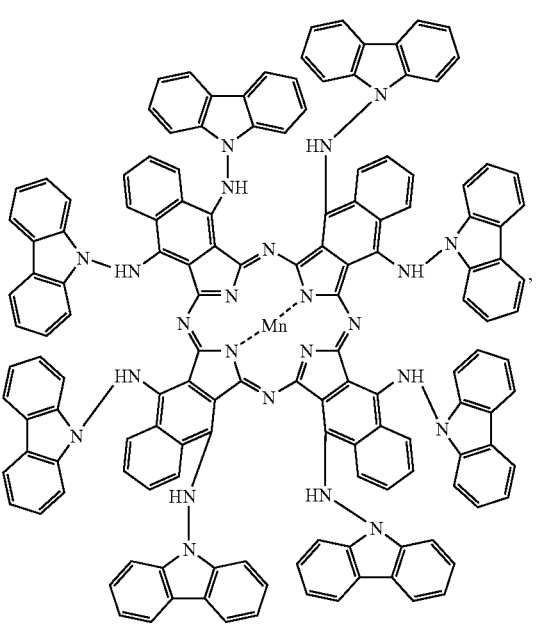

(NC-19)
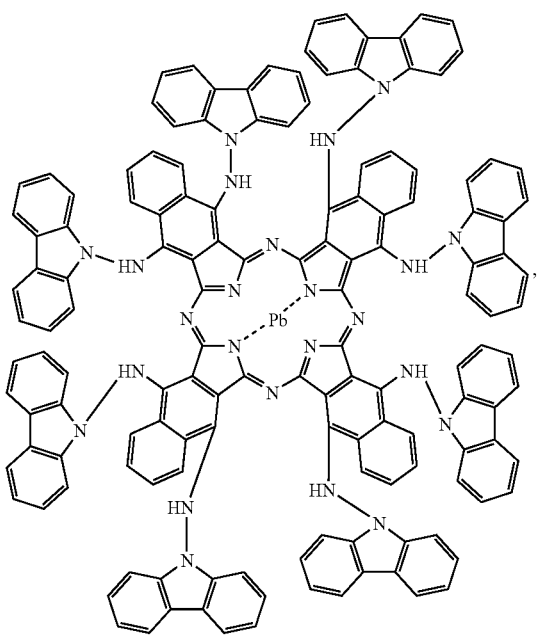
(NC-21)
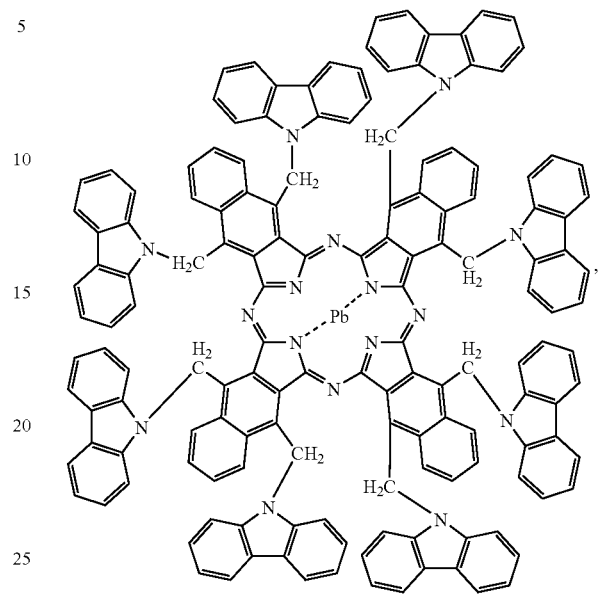
(NC-20)
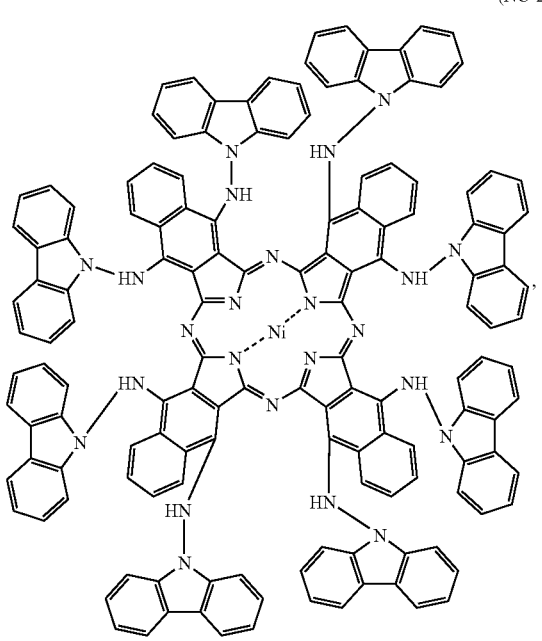
(NC-22)
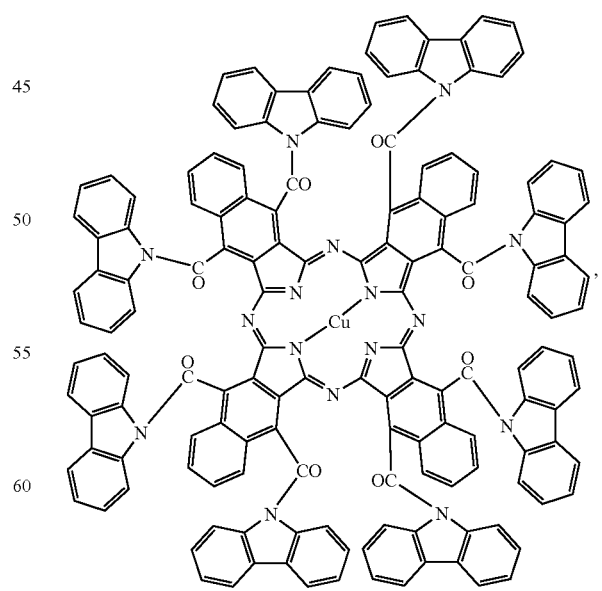

-continued
(NC-23)
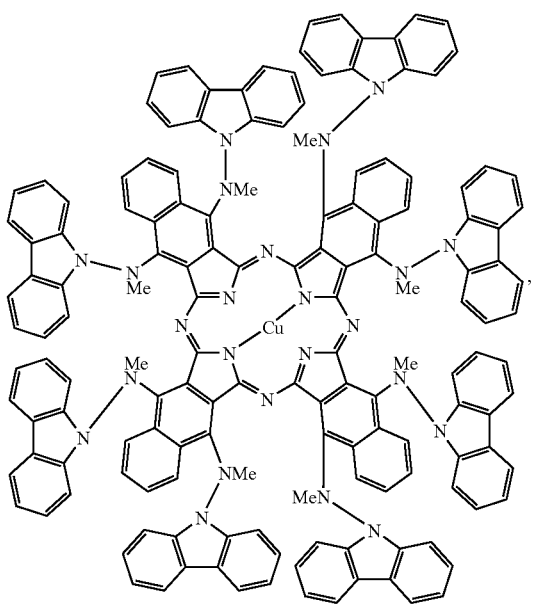
(NC-24)
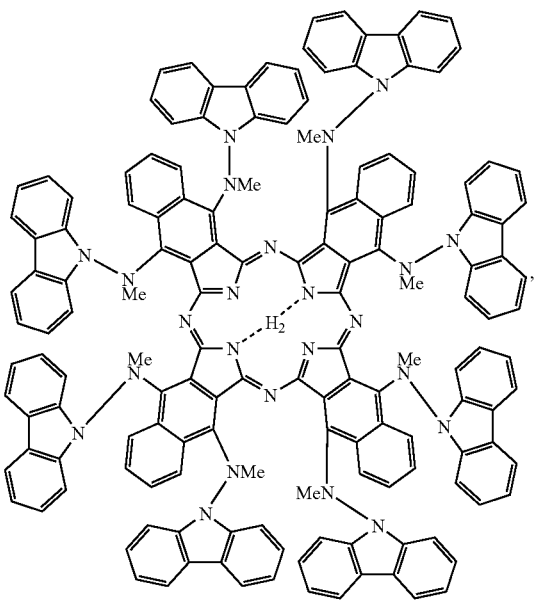
-continued
(NC-25)
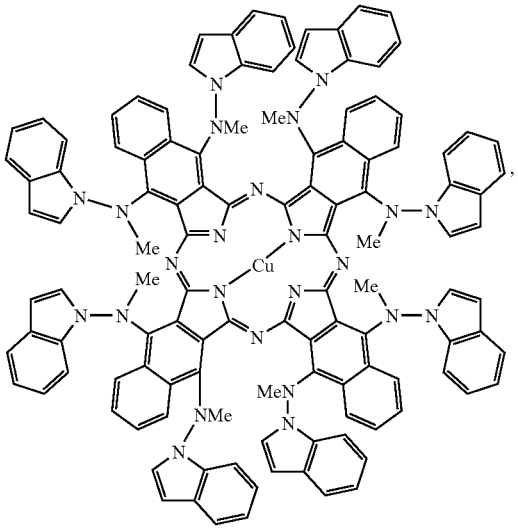
(NC-26)
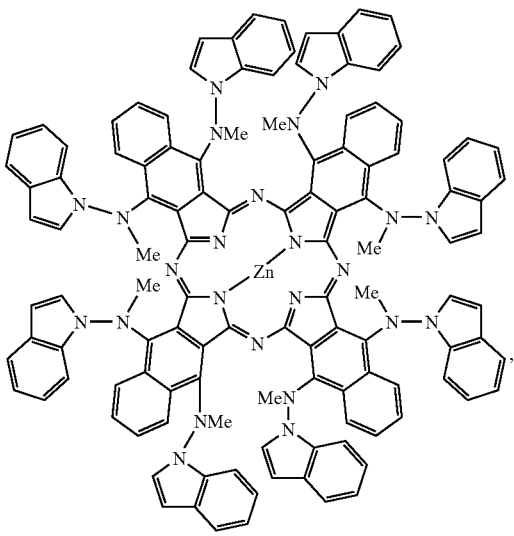
(NC-27)
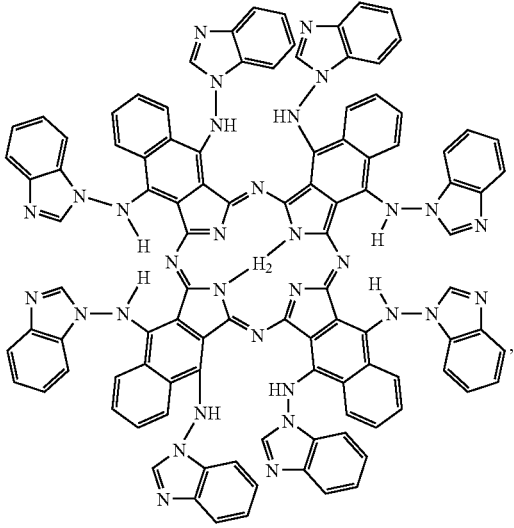

-continued
(NC-28)
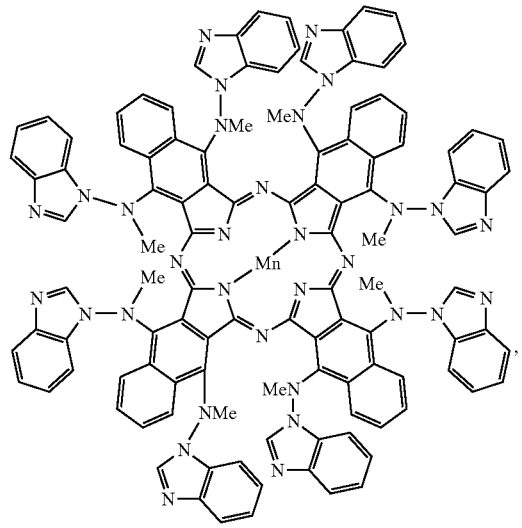
(NC-29)
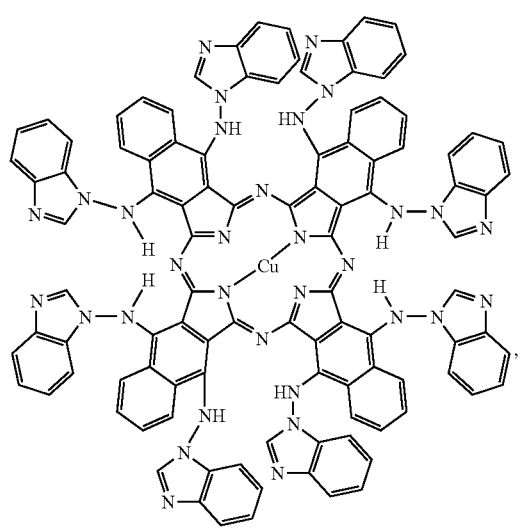
(NC-30)
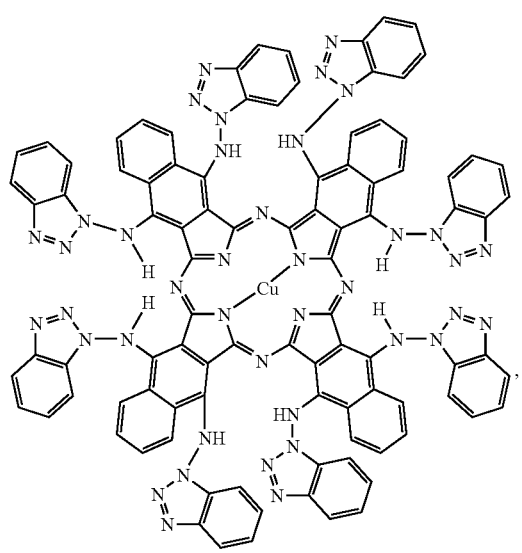
-continued
(NC-31)
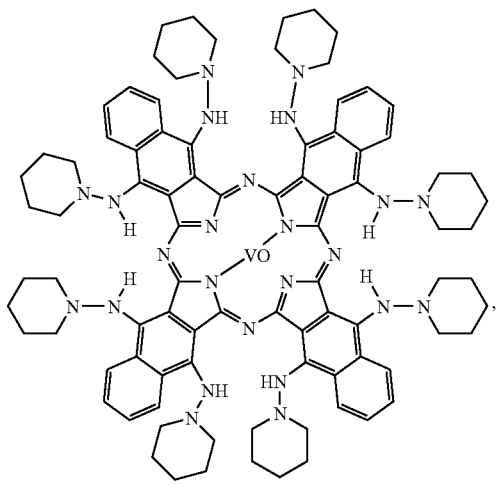
(NC-32)
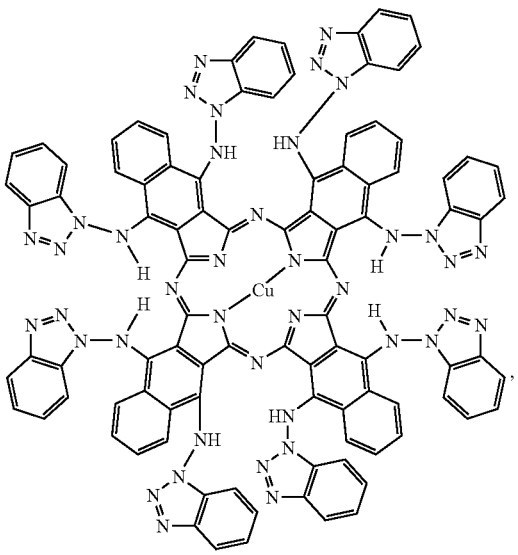

Compounds of Formula (II), (III), (V) or (VI):
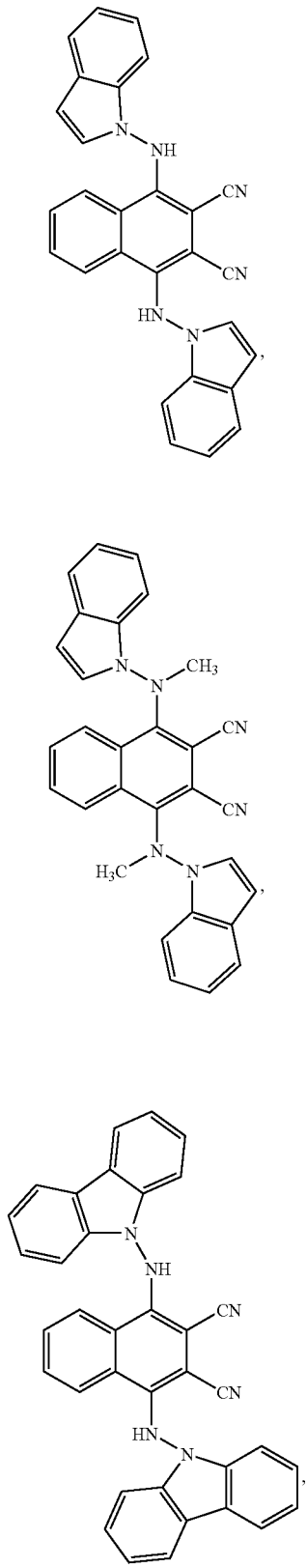
(R-1)
(R-2)
(R-3)
-continued
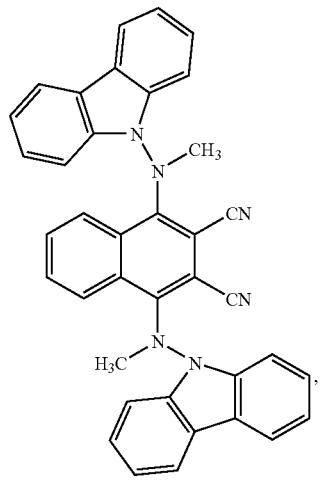
(R-4)
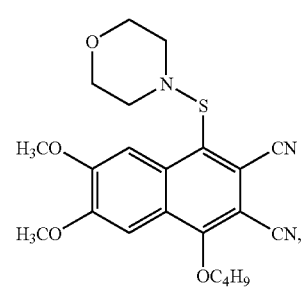
(R-5)
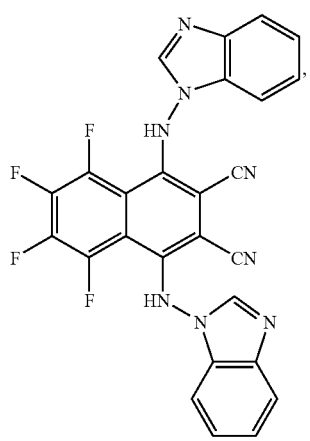
(R-6)
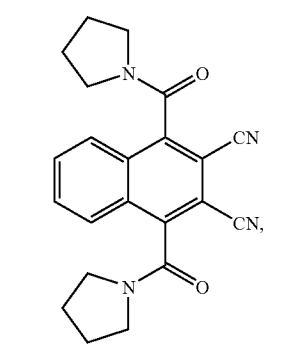
(R-7)

-continued
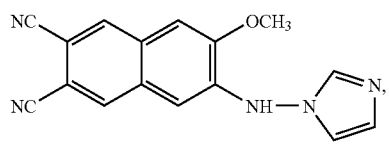
(R-8)
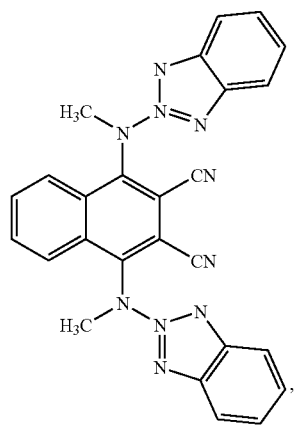
(R-9)
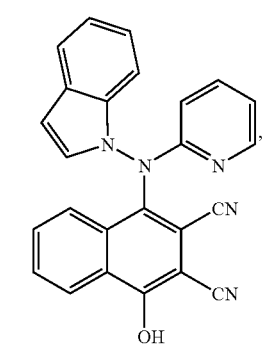
(R-10)
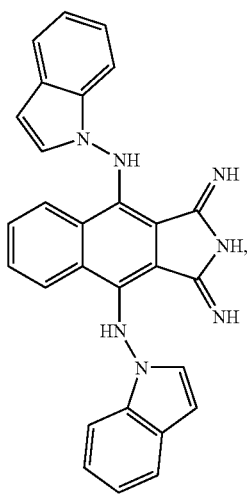
(R-11)
-continued
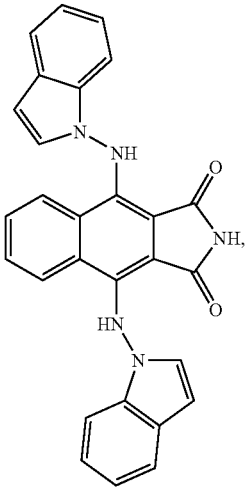
(R-12)
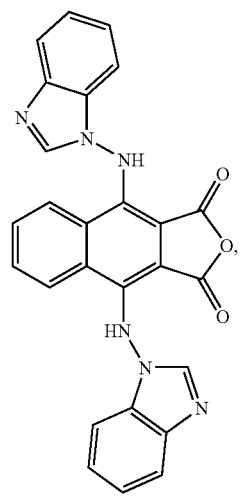
(R-13)
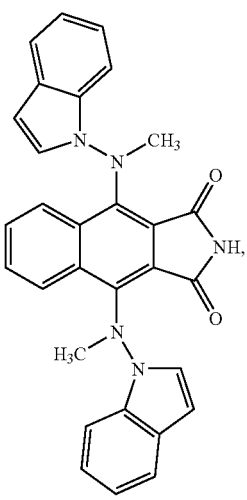
(R-14)

-continued (R-15)

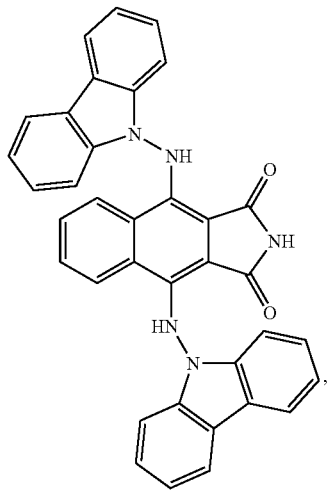

(R-16)

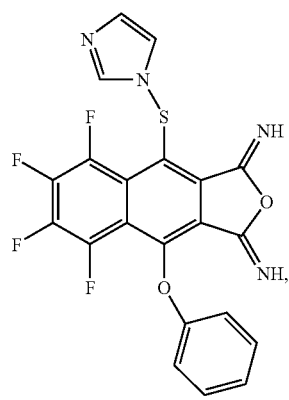

(R-17)

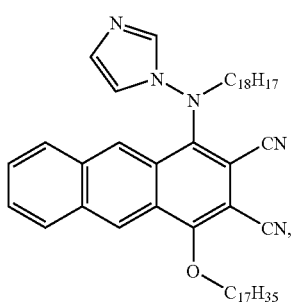

(R-18)

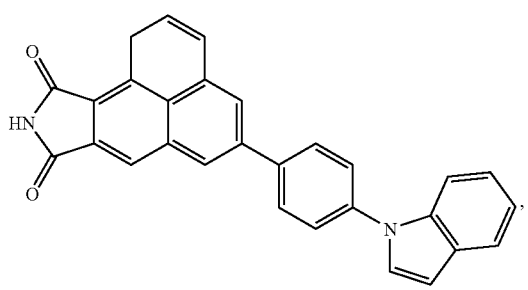

-continued (R-19)

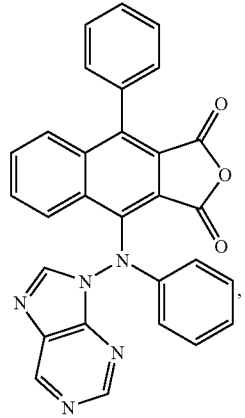

(R-20)

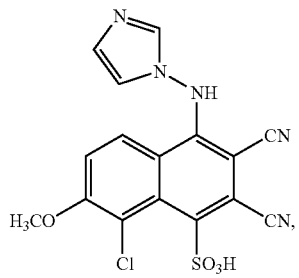

The reaction to obtain a compound of formula (I) or (IV) is attained by mixing a compound of formula (II), (III), (V) or (VI) (component A) and a metal salt (component B) in the presence or absence of a solvent. The metal salt to be used herein is an organic or inorganic compound containing a metal of Groups 1 to 15 and lanthanoid metals. The metal is preferably Li, Na, Mg, Al, K, Ca, Si, Sc, Ti, V, Cr, Mn, Fe, Co, Ni, Cu, Zn, Ge, Ga, Ru, Sn, Rb, Cs, Be, Rh, Pd, Pt, Ba, Cd and Pb; more preferably, Li, Na, Mg, Al, K, Sc, Ti, V, Cr, Mn, Fe, Co, Ni, Cu and Zn; even more preferably, Li, Na, Mg, K, Sc, Ti, V, Cr, Mn, Fe, Co, Ni, Cu and Zn. The component except metal to form the metal salt is preferably a halide ion (e.g., $F^-$, $Cl^-$, $Br^-$), $CN^-$, $SO_4^{2-}$, $HO^-$, $NO_3^-$, $CO_3^{2-}$, a carboxylate ion (e.g., acetate ion, oxalate ion), a sulfonate ion (e.g., methanesulfonate ion, benzenesulfonate ion), a phosphate ion, an alkoxy ion (e.g., methoxy ion, ethoxy ion, isopropoxy ion, phenoxy ion); more preferably, $Cl^-$, $CN^-$, $SO_4^{2-}$, $HO^-$, $CO_3^{2-}$, an acetate ion, or an alkoxy ion; even more preferably, $Cl^-$, $CN^-$, $SO_4^{2-}$, $HO^-$, an acetate ion, or an alkoxy ion.

Regarding the ratio of the starting materials to be reacted, the amount of the component B is preferably from 0.01 to 10 mols, more preferably from 0.1 to 5 mols, even more preferably from 0.2 to 2 mols, still more preferably from 0.25 to 1 mol, relative to one mol of the component A.

The solvent for the reaction includes, for example, amide solvents (e.g., N,N-dimethylformamide, N,N-dimethylacetamide, 1-methyl-2-pyrrolidone), sulfone solvents (e.g., sulforane), sulfoxide solvents (e.g., dimethylsulfoxide), ureide solvents (e.g., tetramethylurea), ether solvents (e.g., dioxane, cyclopentyl methyl ether), ketone solvents (e.g., acetone, cyclohexanone), hydrocarbon solvents (e.g., toluene, xylene), halide solvents (e.g., tetrachloroethane, chlorobenzene), alcohol solvents (e.g., 1-butanol, ethylene glycol, cyclohexanol), pyridine solvents (e.g., pyridine, γ-picoline, 2,6-lutidine); and one or more of these may be used either singly or as combined. Preferred are amide solvents, sulfone solvents, ureide solvents, ether solvents, halide solvents, alcohol solvents, and pyridine solvents; more preferred are amide solvents, sulfone solvents, ether solvents, halide solvents, and alcohol solvents; and even more preferred are amide solvents and alcohol solvents; and most preferred are amide solvents.

The reaction temperature may be generally from 0 to 250° C., preferably from 20 to 200° C., more preferably from 50 to 150° C., even more preferably from 65 to 130° C. Preferably, the reaction temperature is varied during the reaction (for example, at 50° C. in the former half, and at 120° C. in the latter half); and the reaction time may be generally from 5 minutes to 30 hours.

Preferably, a nitrogen-containing compound may be added to the reaction system. Preferred nitrogen-containing compounds are urea, hexamethyldisilazane and ammonia gas (jetting introduction).

The amount of the nitrogen-containing compound to be added may be generally from 0.1 to 100 mols, preferably from 0.1 to 50 mols, more preferably from 0.5 to 20 mols, even more preferably from 1 to 10 mols, still more preferably from 1.5 to 5 mols, further more preferably from 2 to 3 mols, relative to one mol of the component A.

Also preferably, water formed as a side product is taken out of the system during the reaction, for which, for example, preferably employed is a method of evaporating it away singly or along with the solvent used, under reduced pressure or under normal pressure; a method of using an absorbent such as molecular sieve; or a method of using a dehydrating condensing agent such as acetic anhydride. Preferably, the reaction is attained in a closed system.

The compound of formula (II), (III), (V) or (VI) may be obtained by reacting a corresponding halide (e.g., chloride, bromide, fluoride, iodide) or ester [for example, sulfonate (e.g., p-toluenesulfonate, methanesulfonate, trifluoromethanesulfonate), carboxylate (e.g., acetate, trifluoroacetate, benzoate)] (component M) with a heterocyclic compound (component N).

Regarding the ratio of the starting materials to be reacted, the amount of the component N is preferably from 1.5 to 20 mols, more preferably from 2 to 10 mols, even more preferably from 2 to 6 mols, still more preferably from 2 to 3 mols, further more preferably from 2 to 2.5 mols, relative to one mol of the component M. In case where the amount of the component N is 4 mols or less, then it is desirable that a base is made to exist in the reaction system. The base usable herein includes an organic base (e.g., triethylamine, 1,8-diazabicyclo[5.4.0]-7-undecene, 1,4-diazabicyclo[2.2.2]octane, pyridine), and an inorganic base (e.g., sodium hydrogencarbonate, sodium carbonate, potassium carbonate, sodium hydroxide, potassium hydroxide).

The solvent usable in the reaction may be, for example, the above-mentioned solvent. Preferred are amide solvents, sulfone solvents, sulfoxide solvents, ureide solvents, ether solvents, alcohol solvents, and pyridine solvents.

The reaction temperature may be generally from 0 to 250° C., preferably from 0 to 100° C., more preferably from 20 to 80° C.

EXAMPLES

The characteristics of the invention are described more concretely with reference to the following Examples. In the Examples, the material used, its amount and the ratio, the details of the treatment and the treatment process may be suitably modified or changed not overstepping the sprit and the scope of the invention. Accordingly, the invention should not be limitatively interpreted by the Examples mentioned below.

Example 1

52.6 g of the above-mentioned compound, (R-1), 8.1 g of copper chloride, 150 ml of DMF, and 200 ml of tert-butanol were put into a three-neck flask, and stirred with heating at an inner temperature of 90° C. for 3 hours. The solvent was evaporated away from it under reduced pressure, and 3 L of chloroform was added to it, and 3 L of water was added thereto for extraction. The resulting chloroform solution was washed three times, every time by adding 3 L of water thereto, and then concentrated with a rotary evaporator. 500 ml of methanol was added to the residue, and the resulting crystal was taken out through suction filtration, and dried to obtain 37.1 g of the intended, above-mentioned compound, (NC-1) (yield, 68%). Its mass-spectrometry gave $M^+=1,815$ (main peak).

Example 2

54.7 g of the above-mentioned compound, (R-11), 4.2 g of vanadium-oxy trichloride, 50 ml of DMF and 400 ml of tert-butanol were put into a three-neck flask, and stirred with heating at an inner temperature of 85° C. for 3 hours. After this was cooled to room temperature, 500 ml of methanol was added thereto, and the resulting crystal was taken out through suction filtration, and dried to obtain 27.9 g of the intended, above-mentioned compound, (NC-7) (yield, 51%). Its mass-spectrometry gave $M^+=1,819$ (main peak).

Example 3

54.9 g of the above-mentioned compound, (R-12), 6.8 g of tin(II) chloride, 96.8 g of 1,1,1,3,3,3-hexamethyldisilazane, and 500 ml of methanol were put into a three-neck flask, and stirred with heating under reflux for 3 hours. The solvent was evaporated away from it under reduced pressure, and 3 L of chloroform was added to it, and 3 L of water was added thereto for extraction. The resulting chloroform solution was washed three times, every time by adding 3 L of water thereto, and then concentrated with a rotary evaporator. 500 ml of methanol was added to the residue, and the resulting crystal was taken out through suction filtration, and dried to obtain 35.4 g of the intended, above-mentioned compound, (NC-9) (yield, 63%). Its mass-spectrometry gave $M^+=1,872$ (main peak).

Example 4

64.6 g of the above-mentioned compound, (R-3), 10.6 g of manganese(II) chloride, 100 ml of DMF, and 400 ml of tert-butanol were put into a three-neck flask, and stirred with heating under reflux for 5 hours. The solvent was evaporated away from it under reduced pressure, and 3 L of chloroform was added to it, and 3 L of water was added thereto for extraction. The resulting chloroform solution was washed three times, every time by adding 3 L of water thereto, and then concentrated with a rotary evaporator. 500 ml of methanol was added to the residue, and the resulting crystal was taken out through suction filtration, and dried to obtain 27.2 g of the intended, above-mentioned compound, (NC-18) (yield, 41%). Its mass-spectrometry gave $M^+$=2,207 (main peak).

Example 5

52.6 g of the above-mentioned compound, (R-1), 5.8 g of lithium tert-butoxide, 100 ml of DMF, and 300 ml of tert-butanol were put into a three-neck flask, and stirred with heating under reflux for 3 hours. The solvent was evaporated away from it under reduced pressure, and 3 L of chloroform was added to it, and 3 L of water was added thereto for extraction. The resulting chloroform solution was washed three times, every time by adding 3 L of water thereto, and then concentrated with a rotary evaporator. 500 ml of methanol was added to the residue, and the resulting crystal was taken out through suction filtration, and dried to obtain 40.6 g of the intended, above-mentioned compound, (NC-2) (yield, 77%). Its mass-spectrometry gave $M^+$=1,754 (main peak).

Example 6

66.9 g of the above-mentioned compound, (R-15), 8.1 g of copper chloride, 96.8 g of 1,1,1,3,3,3-hexamethyldisilazane, 100 ml of DMF, and 400 ml of tert-butanol were put into a three-neck flask, and stirred with heating under reflux for 5 hours. The solvent was evaporated away from it under reduced pressure, and 3 L of chloroform was added to it, and 3 L of water was added thereto for extraction. The resulting chloroform solution was washed three times, every time by adding 3 L of water thereto, and then concentrated with a rotary evaporator. 500 ml of methanol was added to the residue, and the resulting crystal was taken out through suction filtration, and dried to obtain 27.3 g of the intended, above-mentioned compound, (NC-15) (yield, 41%). Its mass-spectrometry gave $M^+$=2,215 (main peak).

Example 7

24.7 g of 1,4-dichloro-2,3-dicyanonaphthalene and 100 ml of 1-methyl-2-pyrrolidone were put into a three-neck flask, and with stirring and cooling with water, a solution of 79.3 g of 1-aminoindole (produced from indole and hydroxylamine-O-sulfonic acid) and 100 ml of 1-methyl-2-pyrrolidone was dropwise added thereto, taking 30 minutes. After the addition, this was kept stirred for 1 hour as such. Then, this was further stirred for 1 hour at an inner temperature of 50° C., and then for 1 hour at an inner temperature of 90° C. This was cooled to room temperature, and the solvent was evaporated away with an evaporator. 500 ml of ethyl acetate and 500 ml of water were added to the resulting residue for extraction, and the resulting ethyl acetate solution was washed four times, every time with 400 ml of water. Then, this was dried with anhydrous magnesium sulfate and concentrated with a rotary evaporator, and the resulting residue was purified through silica gel column chromatography to obtain 38.6 g of the intended, above-mentioned compound, (R-1) (yield, 88%). Its mass-spectrometry gave $M^+$=438 (main peak).

Example 8

24.7 g of 1,4-dichloro-2,3-dicyanonaphthalene, 48 g of potassium carbonate, and 150 ml of 1-methyl-2-pyrrolidone were put into a three-neck flask, and with stirring and cooling with water, a solution of 32.2 g of N-methylaminoindole and 50 ml of 1-methyl-2-pyrrolidone was dropwise added thereto, taking 30 minutes. After the addition, this was kept stirred for 1 hour as such. Then, this was further stirred for 1 hour at an inner temperature of 50° C., and then for 1 hour at an inner temperature of 110° C. This was cooled to room temperature and concentrated with a rotary evaporator. The resulting residue was extracted with 500 ml of ethyl acetate and 600 ml of water added thereto, and the resulting ethyl acetate solution was washed four times, every time with 400 ml of water. Then, this was dried with anhydrous magnesium sulfate, and concentrated with a rotary evaporator, and the resulting residue was purified through silica gel column chromatography to obtain 35.0 g of the intended, above-mentioned compound, (R-2) (yield, 75%). Its mass-spectrometry gave $M^+$=466 (main peak).

Example 9

26.6 g of 1,4-dichloro-2,3-naphthalenedicarboxyimide, 48 g of potassium carbonate and 150 ml of 1-methyl-2-pyrrolidone were put into a three-neck flask, and with stirring and cooling with water, a solution of 29.1 g of N-aminoindole and 50 ml of 1-methyl-2-pyrrolidone was dropwise added thereto, taking 30 minutes. After the addition, this was kept stirred for 3 hours as such. Then, this was further stirred for 1 hour at an inner temperature of 50° C., and then for 1 hour at an inner temperature of 100° C. This was cooled to room temperature and concentrated with a rotary evaporator. The resulting residue was extracted with 500 ml of ethyl acetate and 600 ml of water added thereto, and the resulting ethyl acetate solution was washed four times, every time with 400 ml of water. Then, this was dried with anhydrous magnesium sulfate, and concentrated with a rotary evaporator. 100 ml of acetic acid was added to the resulting residue, and heated under reflux for 1 hour. This was concentrated with a rotary evaporator, and the resulting residue was extracted with 500 ml of ethyl acetate and 500 ml of aqueous saturated sodium hydrogencarbonate solution added thereto. The resulting ethyl acetate layer was concentrated with a rotary evaporator, and the resulting residue was purified through silica gel column chromatography to obtain 38.9 g of the intended, above-mentioned compound, (R-12) (yield, 85%). Its mass-spectrometry gave $M^+$=457 (main peak).

Example 10

24.7 g of 1,4-dichloro-2,3-dicyanonaphthalene, 48 g of potassium carbonate and 150 ml of 1-methyl-2-pyrrolidone were put into a three-neck flask, and with stirring and cooling with water, a solution of 29.1 g of N-aminoindole and 100 ml of 1-methyl-2-pyrrolidone was dropwise added thereto, taking 30 minutes. After the addition, this was kept stirred for 1 hour as such. Then, this was further stirred for 1 hour at an inner temperature of 50° C., and then for 1 hour at an inner temperature of 80° C. This was cooled to room temperature and concentrated with a rotary evaporator. The resulting residue was extracted with 500 ml of ethyl acetate and 600 ml of water added thereto, and the resulting ethyl acetate solution was washed four times, every time with 400 ml of water. Then, this was dried with anhydrous magnesium sulfate, and concentrated with a rotary evaporator, and the resulting residue was purified through silica gel column chromatography to obtain 39.5 g of the intended, above-mentioned compound, (R-1) (yield, 90%). Its mass-spectrometry gave $M^+$=438 (main peak).

As described in detail hereinabove with reference to its preferred embodiments, the compound of the invention is useful for image-forming materials, IR-sensitive thermal recording materials, optical recording devices and optical film materials, and is effectively used for producing such materials and devices. The compound can be produced according to the simple method of the invention, using the starting material compound of the invention. Accordingly, the industrial applicability of the invention is remarkable.

The present disclosure relates to the subject matter contained in Japanese Patent Application No. 283212/2005 filed on Sep. 29, 2005, which is expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A compound of the following formula (IV):

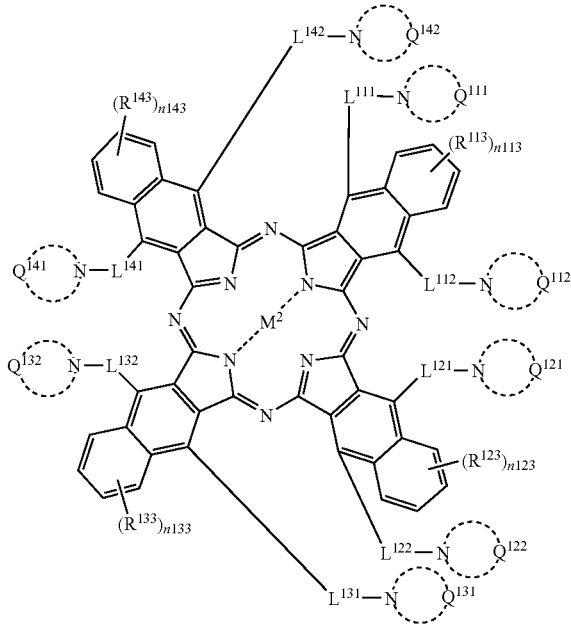

Formula (IV)

$L^{111}$, $L^{112}$, $L^{121}$, $L^{122}$, $L^{131}$, $L^{141}$ and $L^{142}$ each independently represents —O—, —N($R^{211}$)—, —S—, —C($R^{212}$)($R^{213}$)—, —CO—, —CO—N($R^{214}$)—, —SO—, —SO$_2$—, —SO$_2$N($R^{215}$), or a group of their combinations; $R^{211}$, $R^{212}$, $R^{213}$, $R^{214}$ and $R^{215}$ each independently represents a hydrogen atom, an aliphatic group, an aromatic group or a heterocyclic group;

$Q^{111}$, $Q^{112}$, $Q^{121}$, $Q^{122}$, $Q^{131}$, $Q^{132}$, $Q^{141}$ and $Q^{142}$ each independently represents a non-metallic atomic group consisting of atoms selected from C, N, O and S and necessary for forming a 5-membered or 6-membered hetero ring along with the nitrogen atom thereof;

$R^{113}$, $R^{123}$, $R^{133}$ and $R^{143}$ each independently represents a halogen atom, an alkyl group, an aryl group, an alkoxy group, an aryloxy group, an alkylthio group or an arylthio group;

n113, n123, n133 and n143 each independently indicates an integer of from 0 to 4; and $M^2$ represents two hydrogen atoms, two monovalent metal atoms, a divalent metal atom, or a divalent substituted metal atom including a trivalent or tetravalent metal atom.

2. The compound according to claim 1 wherein $L^{111}$, $L^{112}$, $L^{121}$, $L^{122}$, $L^{131}$, $L^{132}$, $L^{141}$ and $L^{142}$ each independently represents —O—, —N($R^{211}$)—, —S—, —C($R^{212}$)($R^{213}$)—, —CO—, —CO—N($R^{214}$)—, —SO—, —SO$_2$— or —SO$_2$N($R^{215}$).

3. The compound according to claim 1 wherein $L^{111}$, $L^{112}$, $L^{121}$, $L^{122}$, $L^{131}$, $L^{132}$, $L^{141}$ and $L^{142}$ each independently represents —O—, —N($R^{211}$)—, —S—, —SO—, —SO$_2$— or —SO$_2$N($R^{215}$).

4. The compound according to claim 1 wherein $L^{111}$, $L^{112}$, $L^{121}$, $L^{122}$, $L^{131}$, $L^{132}$, $L^{141}$ and $L^{142}$ each independently represents —O—, —N($R^{211}$)— or —S—.

5. The compound according to claim 1 wherein $L^{111}$, $L^{112}$, $L^{121}$, $L^{122}$, $L^{131}$, $L^{132}$, $L^{141}$ and $L^{142}$ each independently represents —NH—.

6. The compound according to claim 1 wherein the 5-membered or 6-membered hetero ring is a pyrrolidine ring, a morpholine ring, a 1,3-thiazolidine ring, a thiazole ring, an oxazole ring, a selenazole ring, an imidazole ring, a pyrazole ring, a benzimidazole ring, an indole ring, a benzotriazole ring, a benzothiazole ring, a benzoxazole ring, a purine ring or a carbazole ring.

7. The compound according to claim 1 wherein the 5-membered or 6-membered hetero ring is an indole ring or a carbazole ring.

8. The compound according to claim 1 wherein the 5-membered or 6-membered hetero ring is not substituted.

9. The compound according to claim 1 wherein $R^{113}$, $R^{123}$, $R^{133}$ and $R^{143}$ each independently represents a halogen atom, an alkyl group having from 1 to 20 carbon atoms, an aryl group having from 6 to 20 carbon atoms, an alkoxy group having from 1 to 20 carbon atoms, an aryloxy group having from 6 to 20 carbon atoms, an alkylthio group having from 1 to 20 carbon atoms or an arylthio group having from 6 to 20 carbon atoms.

10. The compound according to claim 1 wherein $R^{113}$, $R^{123}$, $R^{133}$ and $R^{143}$ each independently represents an alkyl group having from 1 to 8 carbon atoms, an aryl group having from 6 to 10 carbon atoms, an alkoxy group having from 1 to 8 carbon atoms, an aryloxy group having from 6 to 10 carbon atoms, an alkylthio group having from 1 to 8 carbon atoms or an arylthio group having from 6 to 10 carbon atoms.

11. The compound according to claim 1 wherein $R^{113}$, $R^{123}$, $R^{133}$ and $R^{143}$ each independently represents an alkoxy group having from 1 to 6 carbon atoms, an aryloxy group having from 6 to 8 carbon atoms, an alkylthio group having from 1 to 6 carbon atoms or an arylthio group having from 6 to 8 carbon atoms.

12. The compound according to claim 1 wherein n113, n123, n133 and n143 are 0.

13. A method for producing a compound of the following formula (IV):

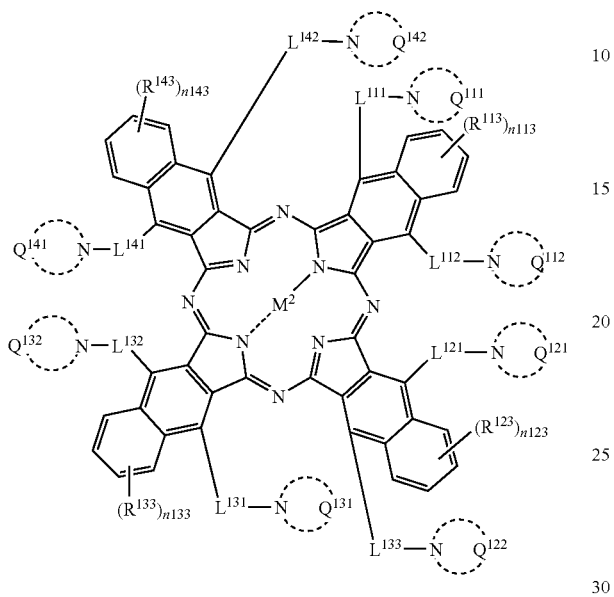

Formula (IV)

wherein $L^{111}$, $L^{112}$, $L^{121}$, $L^{122}$, $L^{131}$, $L^{141}$ and $L^{142}$ each independently represents —O—, —N($R^{211}$)—, —S—, —C($R^{212}$)($R^{213}$)—, —CO—, —CO—N($R^{214}$)—, —SO—, —SO$_2$—, —SO$_2$N($R^{215}$), or a group of their combinations; $R^{211}$, $R^{212}$, $R^{213}$, $R^{214}$ and $R^{215}$ each independently represents a hydrogen atom, an aliphatic group, an aromatic group or a heterocyclic group;

$Q^{111}$, $Q^{112}$, $Q^{121}$, $Q^{122}$, $Q^{131}$, $Q^{132}$, $Q^{141}$ and $Q^{142}$ each independently represents a non-metallic atomic group consisting of atoms selected from C, N, O and S and necessary for forming a 5-membered or 6-membered hetero ring along with the nitrogen atom thereof;

$R^{113}$, $R^{123}$, $R^{133}$ and $R^{143}$ each independently represents a halogen atom, an alkyl group, an aryl group, an alkoxy group, aryloxy group, an alkylthio group or an arylthio group;

n113, n123, n133 and n143 each independently indicates an integer of from 0 to 4; and $M^2$ represents two hydrogen atoms, two monovalent metal atoms, a divalent metal atom, or a divalent substituted metal atom including a trivalent or tetravalent metal atom, comprising converting a compound of formula (V) or (VI) to the compound of formula (IV):

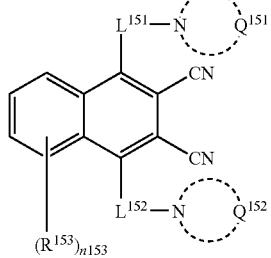

Formula (V)

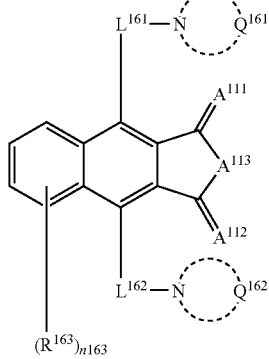

Formula (VI)

wherein $L^{151}$, $L^{152}$, $L^{161}$ and $L^{162}$ each independently represents a divalent group; $Q^{151}$, $Q^{152}$, $Q^{161}$, and $Q^{162}$ each independently represents a non-metallic atomic group necessary for forming a hetero ring along with the nitrogen atom thereof; $R^{153}$ and $R^{163}$ each independently represents a substituent; n153 and n163 each independently indicates an integer of from 0 to 4; and $A^{111}$, $A^{112}$ and $A^{113}$ each independently represents an oxygen atom or NH.

* * * * *